(12) United States Patent
Hakimi et al.

(10) Patent No.: US 11,517,646 B2
(45) Date of Patent: Dec. 6, 2022

(54) SCAFFOLD

(71) Applicant: OXFORD UNIVERSITY INNOVATION LIMITED, Oxford (GB)

(72) Inventors: Osnat Hakimi, Oxford (GB); Pierre-Alexis Mouthuy, Oxford (GB); Nasim Zargar Baboldashti, Oxford (GB); Andrew Carr, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 16/688,676

(22) Filed: Nov. 19, 2019

(65) Prior Publication Data

US 2020/0155724 A1 May 21, 2020

Related U.S. Application Data

(62) Division of application No. 15/026,830, filed as application No. PCT/GB2014/052981 on Oct. 2, 2014, now Pat. No. 10,500,310.

(30) Foreign Application Priority Data

Oct. 4, 2013 (GB) ..................... 1317636

(51) Int. Cl.
*A61L 27/18* (2006.01)
*A61F 13/02* (2006.01)
(Continued)

(52) U.S. Cl.
CPC .............. *A61L 27/38* (2013.01); *A61F 13/02* (2013.01); *A61L 27/18* (2013.01); *A61L 27/56* (2013.01);
(Continued)

(58) Field of Classification Search
None
See application file for complete search history.

(56) References Cited

U.S. PATENT DOCUMENTS

2003/0220700 A1* 11/2003 Hammer ................. A61L 27/18
                                                           623/23.58
2005/0249771 A1   11/2005 Malaviya et al.
(Continued)

FOREIGN PATENT DOCUMENTS

| WO | 2005005609 A2 | 1/2005 |
|----|---------------|--------|
| WO | 2009097534 A1 | 8/2009 |

(Continued)

OTHER PUBLICATIONS

Greiner et al. (Angew. Chem. Int. Ed 2007;46:5670-5703) (Year: 2007).*
(Continued)

*Primary Examiner* — Ernst V Arnold
(74) *Attorney, Agent, or Firm* — Nixon Peabody LLP; Mark J. FitzGerald

(57) ABSTRACT

A scaffold for tissue repair or wound dressing comprising: a material layer; a polymer fibre layer; and an adhesive component between the material layer and the polymer fibre layer, wherein the adhesive component comprises material having a lower melting temperature (Tm) than the material layer and the polymer fibre layer.

14 Claims, 21 Drawing Sheets

Figure 1:
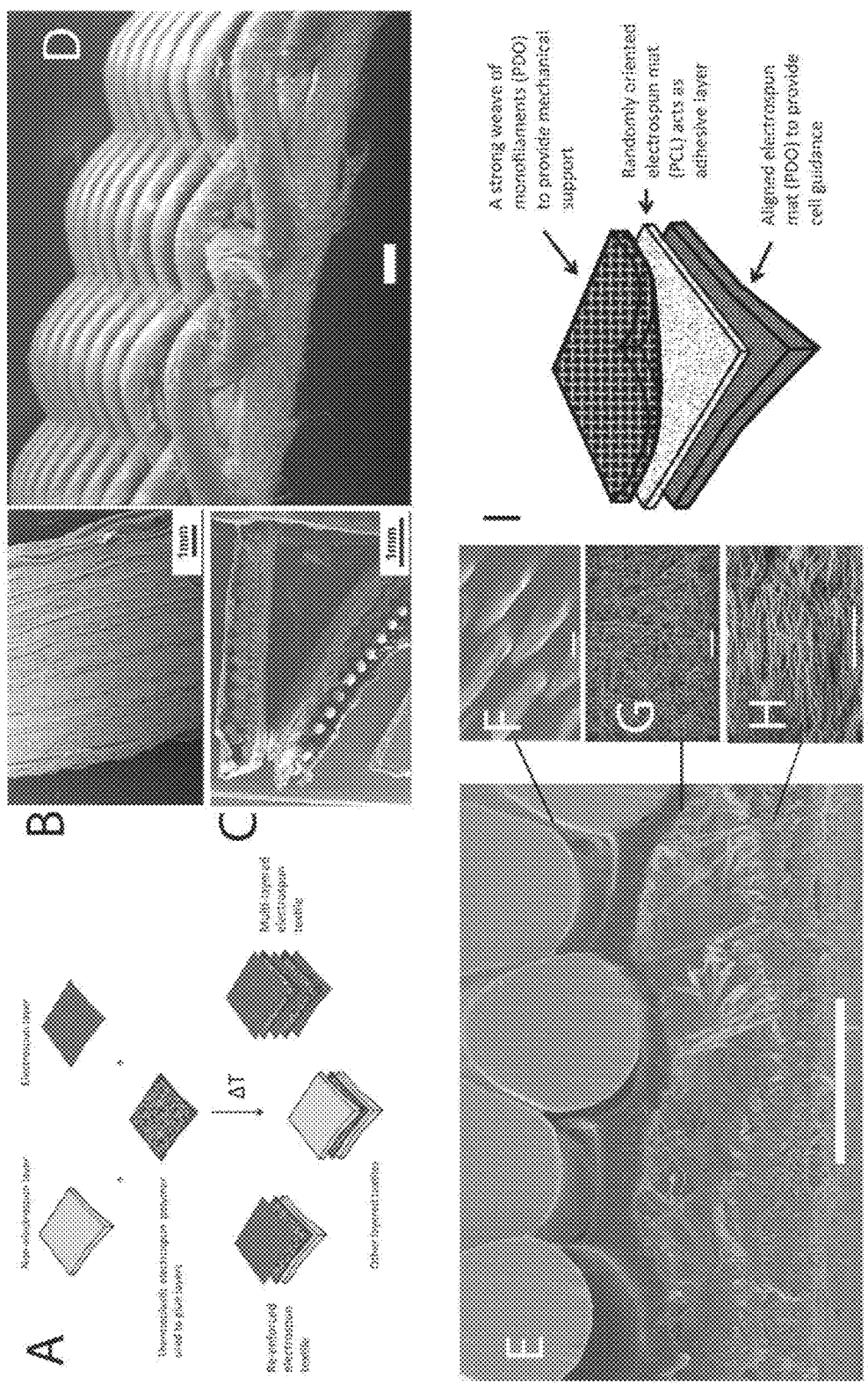

(51) Int. Cl.
    A61L 27/38    (2006.01)
    A61L 27/56    (2006.01)
    A61L 27/58    (2006.01)
(52) U.S. Cl.
    CPC ........... *A61L 27/58* (2013.01); *A61L 2300/64* (2013.01); *A61L 2400/12* (2013.01)

(56) References Cited

U.S. PATENT DOCUMENTS

| | | | |
|---|---|---|---|
| 2009/0152766 A1 | 6/2009 | Rousseau et al. | |
| 2011/0143429 A1 | 6/2011 | Chun et al. | |
| 2012/0239161 A1* | 9/2012 | Datta | A61L 27/18 623/23.72 |

FOREIGN PATENT DOCUMENTS

| | | |
|---|---|---|
| WO | 2011053562 A2 | 5/2011 |
| WO | 2012024370 A2 | 2/2012 |

OTHER PUBLICATIONS

Beason et al., "Fiber-aligned polymer scaffolds for rotator cuff repair in a rat model", Journal of Shoulder and Elbow Surgery 21:245-250 (2012).

Hakimi et al., "Differential growth on sutures of tendon cells derived from torn human rotator cuff", Journal of Biomedical Materials Research Part B: Applied Biomaterials 100B:685-692 (2012).

Ker et al., "Bioprinting of growth factors onto aligned sub-micron fibrous scaffolds for simultaneous control of cell differentiation and alignment", Biomaterials 32:8097-8107 (2011).

Saino et al., "Effect of Electrospun Fiber Diameter and Alignment on Macrophage Activation and Secretion of Proinflammatory Cytokines and Chemokines", Biomacromolecules 12(5):1900-1911 (2011).

Hakimi et al., "An Electrospun Polydioxanone Patch for the Localisation of Biological Therapies During Tendon Repair", European Cells and Materials 24:344-357 (2012).

Xie et al., "Electrospun nanofibers for neural tissue engineering", Nanoscale 2:35-44 (2010).

Yin et al., "The regulation of tendon stem cell differentiation by the alignment of nanofibers", Biomaterials 31:2163-2175 (2010).

Dines et al., "In vitro analysis of an rhGDF-5 suture coating process and the effects of rhGDF-5 on rat tendon fibroblasts", Growth Factors 29(1):1-7 (2011).

Moffat et al., "Novel nanofiber-based scaffold for rotator cuff repair and augmentation", Tissue Engineering Part A 15(1):115-126 (2008).

Poulsen et al., "Protection against glucocorticoid-induced damage in human tenocytes by modulation of ERK, Akt, and forkhead signaling", Endocrinology 152(2):503-514 (2011).

Raghavan et al., "Optimization of Human Tendon Tissue Engineering: Synergistic Effects of Growth Factors for Use in Tendon Scaffold Repopulation", Plastic and Reconstructive Surgery 129(2):479-489 (2012).

Yao et al., "Phenotypic Drift in Human Tenocyte Culture", Tissue Engineering 12(7):1843-1849 (2006).

Chaudhury et al., "Tensile and shear mechanical properties of rotator cuff repair patches", Journal of Shoulder and Elbow Surgery 21:1168-1176 (2012).

Derwin et al., "Commercial Extracellular Matrix Scaffolds for Rotator Cuff Tendon Repair", The Journal of Bone and Joint Surgery 88-A(12):2665-2672 (2006).

* cited by examiner

SCAFFOLD

CROSS-REFERENCE TO RELATED APPLICATIONS

This application is a divisional under 35 U.S.C. § 121 of co-pending U.S. application Ser. No. 15/026,830 filed Apr. 1, 2016, which is a 35 U.S.C. § 371 National Phase Entry Application of International Application No. PCT/GB2014/052981 filed Oct. 2, 2014, which designated the U.S., and which claims priority to GB Application No. 1317636.7 filed Oct. 4, 2013, the contents of each of which are incorporated herein by reference in their entireties.

TECHNICAL FIELD

This invention relates to a biodegradable scaffold for tissue repair, methods of making such scaffolds and uses thereof.

BACKGROUND

Tendon inflammation and age-related degeneration cause shoulder pain that affects more than 30% of the population. Rotator cuff surgery is more and more commonly carried out when conservative treatments fail, with the rate having increased by over 500% since 2001 in the UK. However, the effectiveness of rotator cuff repair surgery has been questioned by clinical and imaging studies, showing a structural failure of the repair in 20-90% of cases. In response to this issue, new repair strategies have been proposed. Among them, the use of degradable synthetic scaffolds have shown high potential as they can combine well-adjusted mechanical properties, biological additives, and minimise risk of infection by completely absorbing in a timely manner. However, these scaffolds are still limited in terms of either biocompatibility or mechanical properties.

Among all the technologies to process those biodegradable polymers into scaffolds, electrospinning has been one of the most promising approaches of this last decade. It produces submicron fibrous structures that can mimic the ultrastructure and orientation of collagen fibrils in the tendon, and even the transition from aligned to random orientation at the tendon to bone insertion site. A number of aligned scaffolds have been shown to direct cell orientation as well as to affect the expression of matrix proteins (Moffat 2009 Tissue Eng Part A, Xie 2010 Nanoscale, Yin 2010 Biomaterials, Beason 2012 J Shoulder Elbow research). A few researchers have also proposed including chemical or biological components into the synthetic scaffold to enhance their performance biologically (Ker 2011 Biomaterials, Dines 2012 Growth Factors). In vitro studies of electrospun structures made of polydioxanone (PDO) have exhibited excellent cellular response and biocompatibility with human tendon cells (Hakimi 2012 J Biomed Mat Res, Hakimi 2012 Eur Cell Mater). Further evaluations have also demonstrated that electrospun materials are likely to cause a lower immune response in vivo compared to the same materials processed into plain sheets. Preliminary efficacy tests of synthetic degradable patches in animal models show good results as well. Electro spun, aligned PCL implanted in a rat model was also well-tolerated, with good cell infiltration up to 8 weeks (Beason, D. P. et al. Special issue on rotator cuff biology and healing Fiber-aligned polymer scaffolds for rotator cuff repair in a rat model. Volume 21, Issue 2, February 2012, Pages 245-250). However, although electrospun materials show excellent cell and tissue response, a major drawback is their poor mechanical properties. This issue has been known for a long time, but has been poorly addressed and often underestimated in musculoskeletal tissue engineering.

Several strategies have been developed to improve the mechanical properties of electrospun scaffolds. Many authors have attempted to improve the material itself through better fibre arrangement, or post-treatment such as cross-linking and bonding but those techniques offer limited mechanical improvement often below the range required. Other approaches include reinforcement with other materials through co-electrospinning methods, multilayering, or by combining the electrospun layer with monofilaments, nonwoven fabrics and woven fabrics. The use of woven fabric (including knitting, braiding, and embroidering) is particularly interesting since, on their own, such matrices have been able to provide mechanical properties equivalent to native tendon. When fabrics are combined with electrospun scaffolds, the main issue reported was the bonding between the two materials. To address this problem, some authors have suggested the use of an adhesive solution in which the fabric is immersed. Fibres are then deposited on the wet surface and the final composite undergoes drying. Others have relied on the presence of residual solvent in the deposited fibres to create a bond with the knitted fabric by electrospinning directly onto it. Chemical and plasma treatments have also been tried in order to improve the bonding.

DESCRIPTION

An aim of the present invention is to provide improved methods for producing layered scaffolds, preferably with suitable mechanical and biological properties.

According to a first aspect of the invention, there is provided a scaffold for tissue repair or wound dressing comprising:
  a material layer;
  a polymer fibre layer; and
  an adhesive component between the material layer and the polymer fibre layer, wherein the adhesive component has a lower melting temperature (Tm) than the material layer and the polymer fibre layer.

The material layer and polymer fibre layer may be bonded to, and via, the adhesive component. The bonding may be by fibre entanglement. The bonding may be by chemical bond, van der waals force, and/or fibre entanglement. During bonding/upon melting the adhesive layer, the molten material of the adhesive layer may penetrate crevices or pores, and/or envelop fibres, of the material layer and polymer fibre layer, which may set in place on cooling the adhesive layer below its Tm.

Advantageously, the lower Tm of the adhesive component allows the adhesive component to be bonded to the material layer and polymer fibre layer by melting at a temperature above its Tm, but without destroying the structure of the material layer or polymer fibre layer. This provides a scaffold suitable as a tissue scaffold for tissue repair or wound dressing. Advantageously, the porosity, pore morphology and/or integrity of the polymer fibre layer may not be compromised by the adhesive or the process of bonding.

The scaffold may be biodegradable. Alternatively, the scaffold may be non-biodegradable. The term "biodegradable" used herein in the context of the scaffold may be considered to be a scaffold formed of material which degrades over time in the environment that it is used, for example in water, a mammalian body or tissue. The scaffold may be capable of being decomposed by living organisms.

The degradation may be by breaking up and/or dissolving. The degradation may be by metabolism, such as enzymatic degradation. The degradation may be by hydrolysis. The degradation may be partial or complete. The timeframe for the initiation of degradation may be between about 5 days and about 2 years. The timeframe for the initiation of degradation may be between about 0 days and about 6 months, or between about 0 days and about 2 years. The timeframe for complete degradation may be dependent on the use or application of the scaffold. The timeframe for complete degradation may be between about 3 days and about 2 years. The timeframe for complete degradation may be between about 3 days and about 6 months. The timeframe for complete degradation may be between about 30 days and about 1 year. The time for complete degradation may be no more than 2 months, 3 months or 4 months.

The degradation rate of the adhesive component may be less/slower than the degradation rate of the polymer fibre layer and/or material layer. The degradation rate of the adhesive component may be at least 80%, 70%, 60% or 50% less/slower than the degradation rate of the polymer fibre layer and/or material layer. This may advantageously prevent premature disintegration of the scaffold.

The scaffold may be biocompatible. The term "biocompatible" used herein may be considered to encompass material that is non-toxic to a mammalian body or tissue in the quantity it is intended to be used. The term "biocompatible" may also be considered to indicate a material that is biodegradable in a mammalian body or tissue. Biocompatible may be considered to be material that is not allergenic or an immunostimulant. Biocompatible may be considered to encompass material that is inert in the body or tissue of a mammal.

The scaffold may be synthetic. The term "synthetic" used herein in the context of a biodegradable synthetic scaffold may be considered to be a non-natural material or origin. For example the material used in the scaffold may not be found in nature. The material of the scaffold may not be partially or completely formed from tissue explant material recovered from an organism.

The material layer may comprise or consist of a polymer. The material layer may comprise or consist of a woven layer. The material layer may comprise or consist of a knitted layer. The material layer may comprise or consist of an embroidered layer. The material layer may comprise or consist of a woven polymer. Alternatively the material layer may comprise or consist of a non-woven polymer fibre. The material layer may comprise substantially the same material and/or structure as the polymer fibre layer. The material layer and/or the polymer fibre layer may comprise or consist of electrospun polymer. The material layer may comprise or consist of electrospun polymer. The material layer may comprise or consist of a matt or mesh of polymer fibres or yarns.

The material layer may comprise or consist of any known tissue scaffold, such as ceramic scaffold. The material layer may be porous. The material layer may be permeable or impermeable. The material layer may comprise or consist of an impermeable membrane. The impermeable membrane may be impermeable to cells, for example to form a barrier to control cell migration, penetration and/or colonisation. The impermeable membrane may be impermeable to liquid. The impermeable membrane may be impermeable to protein or other bioactive molecules. The impermeable membrane may be a polymer sheath. The material layer may comprise a material that has mechanical strength substantially equal or greater than the mechanical strength of the tissue to be repaired, such as tendon. The material layer may comprise a structural support layer or material. The material layer may comprise or consist of a surface of a PDO implant. The material layer may comprise or consist of a surface of a 3D-printed or 3D-cast structure. The material layer may comprise or consist of a membrane. The material layer may comprise or consist of a suture. The material layer may comprise or consist of a surface of an implant, such as a metallic implant.

The material layer and the polymer fibre layer may comprise or consist of the same material or different materials. The material layer and the polymer fibre layer may be derived from the same manufacturing process, such as electrospinning.

Advantageously, the material layer, such as a woven component, may provide mechanical strength to the biodegradable scaffold, for example mechanical strength that is sufficiently high to support tendon tissue during repair.

The term "woven" used herein in the context of the woven component may be considered to be interlaced threads of a material, wherein a series of threads are arranged in one direction and transversed by another series. The threads may be arranged substantially across each other, for example substantially perpendicular. The threads may also alternately cross above and below each other. The woven component may be formed by weaving on a loom. The interlacing may be substantially uniform and/or regular. The woven component may comprise interlaced warp and weft threads. The woven component may comprise any weave pattern, or combinations of weave patterns. The woven component may comprise a plain weave; alternatively a satin or twill weave. The woven component may comprise a 3D weave (multi-layered weave, for example having both vertical and horizontal weave structure). The woven component may comprise embroidery, for example to improve mechanical strength in areas of the weave, for example for suture retention properties.

Where the material layer comprises or consists of polymer, the polymer may comprise or consist of a biocompatible polymer. The polymer may comprise or consist of aliphatic polymer, biodegradable polyesters, or other biodegradable polymers. The polymer may be thermoplastic. The polymer may comprise or consist of PGA (polyglycolide), PLGA (poly(lactic-co-glycolic acid)), PLLA (poly 1-lactic acid), or PDO (polydioxanone). The polymer may comprise or consist of polydioxanone (PDO). The polymer may comprise PCL (polycaprolactone).

The polymer may comprise or consist of any polymer selected from the group comprising poly($\alpha$-hydroxyacids), polylactic or polyglycolic acids, poly-lactide poly-glycolide copolymers, poly-lactide polyethylene glycol (PEG) copolymers, polyesters, poly($\epsilon$-caprolactone), poly(3-hydroxybutyrate), poly(s-caproic acid), poly(p-dioxanone), poly (propylene fumarate), poly(ortho esters), polyol/diketene acetal addition polymers, polyanhydrides, poly(sebacic anhydride) (PSA), poly(carboxybiscarboxyphenoxyphenoxyhexane) (PCPP), poly[bis(p-carboxyphenoxy)methane] (PCPM), copolymers of SA, CPP and CPM poly (amino acids), poly (pseudo amino acids), polyphosphazenes, derivatives of poly[(dichloro) phosphazene], poly[(organo) phosph-azenes] polymers, polyphosphates, polyethylene glycol polypropylene block co-polymers, natural polymers, silk, elastin, chitin, chitosan, fibrin, fibrinogen, polysaccharides (including pectins), alginates, collagen, poly (amino acids), peptides, polypeptides or proteins, co-polymers prepared from the monomers of these polymers, random blends of these polymers or mixtures and combinations thereof.

The material layer may comprise or consist of monofilaments, fibres or yarns. The fibres may be formed by spinning, such as electrospinning. The material layer may comprise or consist of electrospun polymer. The monofilaments, fibres or yarns of the material layer may be between about 3 nm and about 2 mm in diameter. The monofilaments, fibres or yarns of the material layer may be between about 3 nm and about 1 mm in diameter. The monofilaments, fibres or yarns of the material layer may be between about 3 nm and about 500 μm in diameter. The monofilaments, fibres or yarns of the material layer may be between about 3 nm and about 200 μm in diameter. The monofilaments, fibres or yarns of the material layer may be between about 3 nm and about 100 μm in diameter. The monofilaments, fibres or yarns of the material layer may be between about 10 nm and about 200 μm in diameter. The monofilaments, fibres or yarns of the material layer may be between about 100 nm and about 200 μm in diameter. The monofilaments, fibres or yarns of the material layer may be between about 500 nm and about 200 μm in diameter. The monofilaments, fibres or yarns of the material layer may be between about 1 μm and about 200 μm in diameter. The monofilaments, fibres or yarns of the material layer may be between about 1 μm and about 500 μm in diameter. The monofilaments, fibres or yarns of the material layer may be 100 μm or less in diameter. The monofilaments, fibres or yarns of the material layer may be 150 μm or less in diameter. The monofilaments, fibres or yarns of the material layer may be 50 μm or less in diameter. The fibres of the material layer may be substantially aligned.

Advantageously, providing monofilaments, fibres or yarns of the material layer of 100 μm or less in diameter can improve the bonding to the adhesive component.

The material layer may be porous. The material layer may be non-porous. The porosity of the material layer may be between about 0% and about 99% void/volume. The porosity of the material layer may be between about 0% and about 50%. The porosity of the material layer may be between about 50% and about 99%. The porosity of the material layer may be at least about 40%. The porosity of the material layer may be at least about 50%. The porosity of the material layer may be at least about 80%. The porosity of the material layer may be at least about 90%. The porosity of the material layer may be less than about 50%. The porosity of the material layer may be less than about 30%. The porosity of the material layer may be less than about 20%. The average pore size, or substantially each pore size of the material layer may be at least 4 μm in diameter. The average pores size, or substantially each pore size of the material layer may be at least 10 μm in diameter. The average pores size, or substantially each pore size of the material layer may be at least 12 μm in diameter. The average pores size, or substantially each pore size of the material layer may be at least 100 μm in diameter. The average pores size, or substantially each pore size of the material layer may be 100 μm or less in diameter. The average pore size, or substantially each pore size of the material layer may be 1 μm or less in diameter. The average pores size, or substantially each pore size of the material layer may be between about 4 μm and about 100 μm in diameter. The average pores size, or substantially each pore size of the material layer may be between about 8 μm and about 20 μm in diameter.

The polymer fibre layer may be formed from fibres. The fibres of the polymer fibre layer may be formed by spinning, such as electrospinning. The polymer fibre layer may comprise electrospun polymer. The fibres of the polymer fibre layer may be between about 10 nm and about 10 μm in diameter. The fibres of the polymer fibre layer may be between about 5 nm and about 50 μm in diameter. The fibres of the polymer fibre layer may be between about 8 nm and about 20 μm in diameter. The fibres may be substantially orientated in the same direction (e.g. substantially aligned). Alternatively, the fibres may be randomly orientated. The polymer fibre layer may comprise or consist of substantially non-uniform and/or non-regular interlaced or entangled fibres. The fibres of the polymer fibre layer may be mechanically, thermally or chemically bound together. The polymer fibre layer may comprise a mixture of random and aligned fibres. The fibres of the polymer fibre layer may be arranged in a regular and/or uniform pattern. The fibres of the polymer fibre layer may be arranged in a grid. The polymer fibre layer may comprise a layer of polymer comprising nano or micro scale regular or irregular pores, crevices, troughs, and/or extension structures (made for example by 3D printing). The pores, crevices, troughs, and/or extension structures may be spatially arranged in regular patterns, or may be spatially arranged irregularly.

The polymer fibre layer may be non-woven. The term "non-woven" used herein in the context of the polymer fibre layer may be considered to be fibres of material that are not arranged in a woven pattern, or have not been manufactured by weaving, for example in a loom. The term "non-woven" used herein in the context of the polymer fibre layer may be considered to be a layer of material that is made differently from weaving, such as electrospinning or 3D-printing.

Spinning, particularly electrospinning, advantageously allows the entrapment of factors (for example, bioactive molecules such as growth factors or vitamins) during the production of the scaffold, thus incorporating the active ingredients within the fibres. Electrospinning can beneficially provide a high specific surface area, for example for active delivery. A high surface area offers a better release profile of bioactive agents and control over the release. Active agents may be incorporated before (in the polymer solution) or after electrospinning (by adsorption, facilitated by the high specific surface area). Spinning, particularly electrospinning, advantageously allows production of fibres that have dimensions similar to the extracellular matrix, thereby mimicking the cellular environment, providing cell signalling and guidance via topographical features.

The polymer fibre layer may comprise or consist of a polymer, such as a biocompatible polymer. The polymer fibre layer may comprise or consist of aliphatic polymer, biodegradable polyesters, or other biodegradable polymers. The polymer may be thermoplastic. The polymer fibre layer may comprise or consist of PGA (polyglycolide), PLGA (poly(lactic-co-glycolic acid)) PLLA (poly 1-lactic acid), or PDO (polydioxanone). The polymer fibre layer may comprise or consist of polydioxanone (PDO).

The polymer fibre layer may comprise or consist of any polymer selected from the group comprising poly(α-hydroxyacids), polylactic or polyglycolic acids, poly-lactide poly-glycolide copolymers, poly-lactide polyethylene glycol (PEG) copolymers, polyesters, poly(ε-caprolactone), poly (3-hydroxy-butyrate), poly(s-caproic acid), poly(p-dioxanone), poly(propylene fumarate), poly(ortho esters), polyol/diketene acetal addition polymers, polyanhydrides, poly(sebacic anhydride) (PSA), poly(carboxybiscarboxyphenoxyphenoxyhexane) (PCPP), poly[bis(p-carboxyphenoxy)methane] (PCPM), copolymers of SA, CPP and CPM poly (amino acids), poly (pseudo amino acids), polyphosphazenes, derivatives of poly[(dichloro) phosphazene], poly [(organo) phosph-azenes] polymers, polyphosphates, polyethylene glycol polypropylene block co-polymers, natural polymers, silk, elastin, chitin, chitosan, fibrin, fibrinogen, polysaccharides (including pectins), alginates, collagen, poly (amino acids), peptides, polypeptides or proteins, copolymers prepared from the monomers of these polymers, random blends of these polymers or mixtures and combinations thereof.

The polymer fibre layer may be porous, such as sufficiently porous to allow passage of bioactive molecules, or proteins, or cells, or blood vessels. The average pore size, or substantially each pore size of the polymer fibre layer may be at least 4 μm in diameter. The average pore size, or substantially each pore size of the polymer fibre layer may be at least 10 μm in diameter. The average pore size, or substantially each pore size of the polymer fibre layer may be at least 12 μm in diameter. The average pore size, or substantially each pore size of the polymer fibre layer may be at least 100 μm in diameter. The average pore size, or substantially each pore size of the polymer fibre layer may be at least 150 μm in diameter. The average pore size, or substantially each pore size of the polymer fibre layer may be at least 500 μm in diameter. The average pore size, or substantially each pore size of the polymer fibre layer may be at least 1 mm in diameter. The average pore size, or substantially each pore size of the polymer fibre layer may be 100 μm or less in diameter. The average pore size, or substantially each pore size of the polymer fibre layer may be 1 μm or less in diameter. The average pore size, or substantially each pore size of the polymer fibre layer may be between about 4 μm and about 100 μm in diameter. The average pore size, or substantially each pore size of the polymer fibre layer may be between about 8 μm and about 20 μm in diameter. The average pore size, or substantially each pore size of the polymer fibre layer may be between about 1 nm and about 500 μm in diameter. The average pore size, or substantially each pore size of the polymer fibre layer may be sufficiently large enough to permit cell passage and/or blood vessel growth. The porosity of the polymer fibre layer may be between about 0% and about 99% void/volume. The porosity of the polymer fibre layer may be between about 0% and about 50%. The porosity of the polymer fibre layer may be between about 50% and about 99%. The porosity of the polymer fibre layer may be at least about 40%. The porosity of the polymer fibre layer may be at least about 50%. The porosity of the polymer fibre layer may be at least about 80%. The porosity of the polymer fibre layer may be at least about 90%. The porosity of the polymer fibre layer may be less than about 50%. The porosity of the polymer fibre layer may be less than about 30%.

Advantageously, a highly porous polymer fibre layer allows effective trapping of cells and/or protein and blood vessel ingrowth.

The material layer and the polymer fibre layer may comprise substantially the same material, such as substantially the same biocompatible polymer. Alternatively, the polymer layer and the polymer fibre layer may comprise different material. The different material may have substantially similar properties, such as substantially the same melting temperature. Substantially the same melting temperature may be within about 15° C. difference in Tm, within about 10° C. difference in Tm, within about 5° C. difference in Tm, or within about 2° C. difference in Tm. Substantially the same melting temperature may be within about 1° C. difference in Tm.

The adhesive component may comprise or consist of a polymer. The adhesive component may comprise or consist of a biocompatible polymer. The adhesive component may comprise or consist of a thermoplastic polymer. The adhesive component may comprise or consist of a thermoplastic, biocompatible polymer. The adhesive component may comprise or consist of a biocompatible, electrospun polymer. The adhesive component may comprise or consist of a thermoplastic, biocompatible, electrospun polymer. The adhesive component may comprise or consist of copolymers, such as PCL with one or more other polymer. The adhesive component may comprise or consist of polymer having a Tm of 110° C. or less. The adhesive component may comprise or consist of polymer having a Tm of between about 65° C. and about 70° C. The adhesive component may comprise or consist of any polymer having a Tm less than the Tm of the material layer and polymer fibre layer. The adhesive component may comprise or consist of polycaprolactone (PCL). The adhesive component may comprise or consist of PGLA. The adhesive component may comprise or consist of PDO.

The adhesive component may comprise or consist of fibre. The adhesive component may comprise or consist of powder. The adhesive component may comprise or consist of sheet material, such as perforated sheet material. The adhesive component may comprise or consist of electrospun polymer. The fibre of the adhesive component may be formed by spinning, such as electrospinning. The fibre of the adhesive component may be formed by spinning, such as electrospinning, onto a grid. The grid may be patterned with regular voids. The fibres of the adhesive component may be substantially aligned. The fibres of the adhesive component may be substantially arranged in a grid pattern. The fibres of the adhesive component may be substantially meshed. The fibres of the adhesive component may be substantially entangled.

The fibres of the adhesive component may be between about 10 nm and about 10 μm in diameter. The fibres of the adhesive component may be between about 1 nm and about 2 mm in diameter. The fibres of the adhesive component may be between about 5 nm and about 50 μm in diameter. The fibres of the adhesive component may be between about 8 nm and about 20 μm in diameter.

The adhesive component may be porous, such as sufficiently porous to allow passage of bioactive molecules, or proteins, or cells, or blood vessels. The adhesive component may be non-porous. The average pore size, or substantially each pore size of the adhesive component may be at least 4 μm in diameter. The average pores size, or substantially each pore size of the adhesive component may be at least 10 μm in diameter. The average pore size, or substantially each pore size of the adhesive component may be at least 12 μm in diameter. The average pore size, or substantially each pore size of the adhesive component may be at least 100 μm in diameter. The average pore size, or substantially each pore size of the adhesive component may be at least 150 μm in diameter. The average pore size, or substantially each pore size of the adhesive component may be at least 500 μm in diameter. The average pores size, or substantially each pore size of the adhesive component may be at least 1 mm in diameter. The average pore size, or substantially each pore size of the adhesive component may be 100 μm or less in diameter. The average pore size, or substantially each pore size of the adhesive component may be 1 μm or less in diameter. The average pore size, or substantially each pore size of the adhesive component may be between about 4 μm and about 100 μm in diameter. The average pore size, or substantially each pore size of the adhesive component may be between about 8 μm and about 20 μm in diameter. The average pore size, or substantially each pore size of the adhesive component may be sufficiently large enough to permit cell passage and/or blood vessel growth.

Advantageously, the adhesive layer may be produced by electrospinning, to allow a continuity of the porous structure between the different layers. If thin enough, the heat-treated/bonded adhesive layer will preserve its initial porous morphology, whereas thicker layers may form a non-porous film upon melting/solidification.

The adhesive component may be a sheet of polymer, such as a non-porous sheet of polymer.

The adhesive component may have a melting temperature (Tm) of less than about 350° C. or 300° C. The adhesive component may have a melting temperature (Tm) of less than about 200° C. The adhesive component may have a melting temperature (Tm) of less than about 150° C. The adhesive component may have a melting temperature (Tm) of less than about 100° C. The adhesive component may have a melting temperature (Tm) of less than about 70° C. The adhesive component may have a melting temperature (Tm) of less than about 68° C., or about 65° C., or less. The adhesive component may have a melting temperature (Tm) of at least about 45° C. The adhesive component may have a melting temperature (Tm) of between about 45° C. and about 350° C. The adhesive component may have a melting temperature (Tm) of between about 45° C. and about 200° C. The adhesive component may have a melting temperature (Tm) of between about 45° C. and about 100° C. The adhesive component may have a melting temperature (Tm) of between about 45° C. and about 70° C.

The material layer may have a melting temperature (Tm) of at least about 70° C. The material layer may have a melting temperature (Tm) of at least about 80° C., or at least about 85° C. The polymer material layer may have a melting temperature (Tm) of at least about 90° C., about 95° C., about 100° C., about 105° C., about 110° C., or about 110° C., or more. The material layer may have a melting temperature (Tm) of less than about 500° C. The material layer may have a melting temperature (Tm) of less than about 400° C. The material layer may have a melting temperature (Tm) of less than about 300° C. The material layer may have a melting temperature (Tm) of less than about 200° C. The material layer may have a melting temperature (Tm) of between about 70° C. and about 450° C. The material layer may have a melting temperature (Tm) of between about 70° C. and about 400° C. The material layer may have a melting temperature (Tm) of between about 300° C. and about 400° C. The material layer may have a melting temperature (Tm) of between about 100° C. and about 400° C. The material layer may have a melting temperature (Tm) of between about 150° C. and about 450° C. The material layer may have a melting temperature (Tm) of between about 180° C. and about 400° C. The material layer may have a melting temperature (Tm) of between about 70° C. and about 150° C.

The polymer fibre layer may have a melting temperature (Tm) of at least about 70° C. The polymer fibre layer may have a melting temperature (Tm) of at least about 80° C., or at least about 85° C. The polymer fibre material layer may have a melting temperature (Tm) of at least about 90° C., about 95° C., about 100° C., about 105° C., about 110° C., or about 110° C., or more. The polymer fibre layer may have a melting temperature (Tm) of less than about 500° C. The polymer fibre layer may have a melting temperature (Tm) of less than about 400° C. The polymer fibre layer may have a melting temperature (Tm) of less than about 300° C. The polymer fibre layer may have a melting temperature (Tm) of less than about 200° C. The polymer fibre layer may have a melting temperature (Tm) of between about 70° C. and about 450° C. The polymer fibre layer may have a melting temperature (Tm) of between about 70° C. and about 400° C. The polymer fibre layer may have a melting temperature (Tm) of between about 300° C. and about 400° C. The polymer fibre layer may have a melting temperature (Tm) of between about 100° C. and about 400° C. The polymer fibre layer may have a melting temperature (Tm) of between about 150° C. and about 450° C. The polymer fibre layer may have a melting temperature (Tm) of between about 180° C. and about 400° C. The polymer fibre layer may have a melting temperature (Tm) of between about 70° C. and about 150° C.

The scaffold may comprise or consist of two or more layers of the material layer and/or polymer fibre layer. The scaffold may comprise or consist of ten or more layers of the material layer and/or polymer fibre layer. The scaffold may comprise or consist of fifty or more layers of the material layer and/or polymer fibre layer. The scaffold may comprise or consist of one hundred or more layers of the material layer and/or polymer fibre layer. The layers of material layer and polymer fibre layer may be alternate, for example with a layer of the polymer fibre layer between each layer of material layer, or vice versa. Multiple layers of material layer and polymer fibre layer may be provided either in alternate layers, or in any sequence of regular or irregular layering. Each layer may be bonded by an adhesive component therebetween.

The scaffold may comprise a PDO layer, preferably an electrospun PDO layer; and a PCL adhesive layer, preferably an elecrospun PCL layer; and a second PDO layer, preferably a woven PDO layer.

The scaffold may be between about 50 μm and about 10 cm in thickness. The scaffold may be between about 50 μm and about 2 cm in thickness. The scaffold may be between about 50 μm and about 1 cm in thickness. The scaffold may be between about 50 μm and about 10 mm in thickness. The scaffold may be between about 200 μm and about 10 mm in thickness The scaffold may be between about 50 μm and about 1 mm in thickness. The scaffold may be between about 0.1 mm and about 1 mm in thickness.

The scaffold may be between about 50 μm and about 500 μm in thickness. The scaffold may be between about 100 μm and about 500 μm in thickness. The scaffold may be between about 200 μm and about 300 μm in thickness. The scaffold may be between about 230 μm and about 290 μm in thickness. The scaffold may be at least about 50 μm or at least about 150 μm in thickness.

The scaffold may have an area of at least 0.1 cm$^2$ in size. The scaffold may have an area of at least 1 cm$^2$ in size. The scaffold may have an area of at least 10 cm$^2$ in size. The scaffold may have an area of at least 20 cm$^2$ in size. The scaffold may have an area of at least 25 cm$^2$ in size.

The material layer may be between about 20 μm and about 1 cm in thickness. The material layer may be between about 20 μm and about 5 mm in thickness. The material layer may be between about 20 μm and about 1 mm in thickness. The material layer may be between about 20 μm and about 100 μm in thickness. The polymer fibre layer may be between about 20 μm and about 1 cm in thickness. The polymer fibre layer may be between about 20 μm and about 5 mm in thickness. The polymer fibre layer may be between about 20 μm and about 1 mm in thickness. The polymer fibre layer may be between about 20 μm and about 100 μm in thickness. The adhesive component may be between about 20 μm and about 10 mm in thickness. The adhesive component may be between about 20 μm and about 1 mm in thickness. The adhesive component may be between about 20 μm and about 0.1 mm in thickness.

The scaffold may have a tensile strength of at least equal to or greater than tendon for example measured using a Zwick machine at a rate of 0.5 mm/min until failure. The scaffold may have a tensile strength of at least 30 MPa for example measured using a Zwick machine at a rate of 0.5 mm/min until failure. The scaffold may have a tensile strength of at least 62 MPa for example measured using a Zwick machine at a rate of 0.5 mm/min until failure. The scaffold may have a tensile strength of at least 80 MPa for example measured using a Zwick machine at a rate of 0.5 mm/min until failure. The scaffold may have a tensile strength of at least 100 MPa for example measured using a Zwick machine at a rate of 0.5 mm/min until failure.

The biodegradable scaffold may have breaking strain of at least equal to or greater than tendon, for example measured using a Zwick machine at a rate of 0.5 mm/min until failure. The biodegradable scaffold may have breaking strain of at least 30%, for example measured using a Zwick machine at a rate of 0.5 mm/min until failure. The biodegradable scaffold may have breaking strain of at least 38%, for example measured using a Zwick machine at a rate of 0.5 mm/min until failure. The biodegradable scaffold may have breaking strain of at least 45%, for example measured using a Zwick machine at a rate of 0.5 mm/min until failure. The biodegradable scaffold may have breaking strain of at least 55%, for example measured using a Zwick machine at a rate of 0.5 mm/min until failure.

Advantageously, the scaffold of the invention retains a highly textured surface. A further advantage is that the scaffold is flexible and elastic, providing suitable properties for tissue repair, such as tendon repair. The morphology of the scaffold may be substantially similar to tendon.

The scaffold may be detectable in vivo by ultrasound.

The scaffold may comprise one or more agents dispersed or impregnated therein, or seeded thereon. The scaffold may be at least partially coated, or fully coated, with an agent. The material layer and/or polymer fibre layer may comprise one or more agents dispersed or impregnated therein, or seeded thereon. The adhesive component may comprise one or more agents dispersed or impregnated therein, or seeded thereon. The one or more agents may me provided during or after manufacture. The one or more agents may be incorporated into the scaffold by soaking the scaffold in an agent, or composition comprising an agent.

The one or more agents may be an active agent, such as a bioactive molecule. The agent may comprise an agent selected from any of the group comprising an antibiotic; an anti-inflammatory; morphogen; a therapeutic; an anti-coagulant; a nutrient, such as vitamin; a growth-factor; and a chemo-attractant; an analgesic; an anti-mycotic; an antioxidant; a signalling molecule; active peptide, such as binding motif RGD; platelet rich plasma; fibrin glue; ECM proteins; and non-adhesive proteins, such as lubricin; or combinations thereof.

The biodegradable scaffold may comprise cells. The cells may comprise mammalian, such as human. The cells may originate from the patient for which the biodegradable scaffold may be used. The cells may comprise stem cells. The cells may comprise progenitor cells. The cells may comprise parenchymal cells and/or non-parenchymal cells. The cells may comprise immune cells. The cells may comprise inflammatory cells. The cells may comprise cells that are typical components of tendon, bone, cartilage, or ligament tissue. The cells may comprise tenocytes. The cells may be induced pluripotent stem cells. The cells may be fibroblasts.

The scaffold may be substantially free from residual solvent, such as organic solvents.

According to another aspect of the invention, there is provided a scaffold in accordance with the invention herein, for use as a medicament.

The use may be for repair or replacement of damaged (such as torn) or degenerated tendon in a subject. The use may be for repair or replacement of damaged or degenerated ligament, bone and/or cartilage. The use may be for rotator cuff repair. The use may be for subacromial decompression. The use may be for chronic degenerative rotator cuff tendinopathy. The use may be for a partial or full thickness supraspinatus tear. The use may be for wound dressing. The use may be for reducing inflammation around a damaged tendon. The use may be encouraging healing. The use may be to augment tendon tissue to bone. The use may be for localising therapeutic agent delivery, such as platelet rich plasma (PRP) or platelet poor plasma (PPP), to the site of tissue damage.

The subject may be a mammalian subject. The mammalian subject may be a human subject.

According to another aspect of the invention, there is provided a scaffold in accordance with the invention herein, for use as a wound dressing.

According to another aspect of the invention, there is provided the use of the scaffold in accordance with the invention herein, as a filter. The filter may be an environmental filter, a water filter, sewage filter, air filter or gas filter. The filter may be for a gas mask or gas sensor. The filter may be a nanoparticle filter. The filter may be a bacterial filter. The filter may be degradable. The filter may comprise average pore sizes of <0.2 μm.

According to another aspect of the invention, there is provided the use of the scaffold in accordance with the invention herein, as packaging.

According to another aspect of the invention, there is provided a method of treatment for a condition requiring or benefiting from the repair or replacement of damaged or degenerated tendon, ligament, bone and/or cartilage, comprising the use of the scaffold in accordance the invention herein to repair, supplement or replace tissue.

The tissue may comprise tendon, ligament, bone and/or cartilage.

According to another aspect of the invention, there is provided a method of treatment for a wound, comprising the application of the scaffold in accordance the invention herein to the wound.

The wound may be from a burn, cut, graze, tear, infection, or inflammation. The wound may be a skin wound, or wound of another tissue or organ.

According to another aspect of the invention, there is provided a method of producing a scaffold for tissue repair comprising the steps of:
  laying a material layer onto a polymer fibre layer with an adhesive component therebetween to form a layered material; and
  heating the layered material to a temperature above the melting temperature of the adhesive component and then cooling the layered material to a temperature below the melting temperature of the adhesive component, thereby bonding the layered material together to form a scaffold.

According to another aspect of the invention, there is provided a method of producing a scaffold for tissue repair comprising the steps of:
- laying a material layer with an adhesive component to form a layered material; and
- heating the layered material to a temperature above the melting temperature of the adhesive component and then cooling the layered material to a temperature below the melting temperature of the adhesive component, thereby bonding the layered material together; and
- laying the layered material on a polymer fibre layer; and heating to a temperature above the melting temperature of the adhesive component and then cooling the layered material to a temperature below the melting temperature of the adhesive component, thereby bonding the layered material to the polymer fibre layer to form the scaffold.

According to another aspect of the invention, there is provided a method of producing a scaffold for tissue repair comprising the steps of:
- laying a polymer fibre layer with an adhesive component to form a layered material; and
- heating the layered material to a temperature above the melting temperature of the adhesive component and then cooling the layered material to a temperature below the melting temperature of the adhesive component, thereby bonding the layered material together; and
- laying the layered material on a material layer; and heating to a temperature above the melting temperature of the adhesive component and then cooling the layered material to a temperature below the melting temperature of the adhesive component, thereby bonding the layered material to the material layer to form the scaffold.

Pressure may be applied to the layered material in order to press the layers together during the heating and cooling. The pressure may be between about 0.1 psi and about 50 psi. The layers may be clamped together during the heating and cooling.

The layered material may be heated to a temperature of less than the melting temperature (Tm) of the material layer and polymer fibre layer. The layered material may be heated to a temperature of about 80° C. The layered material may be heated to a temperature of at least 60° C., or 80° C. The layered material may be heated to a temperature of between about 60° C. and about 100° C.

The layered material may be heated for about 60 seconds prior to cooling. The layered material may be heated for at least about 30 seconds, or 40 seconds, prior to cooling. The layered material may be heated for at least about 60 seconds, prior to cooling. The layered material may be heated for at least about 120 seconds, prior to cooling. The layered material may be heated for at least about 3 minutes prior to cooling. The layered material may be heated for at least about 5 minutes prior to cooling. The layered material may be heated for at least about 1 hour, prior to cooling. The layered material may be heated for at least about 3 hours prior to cooling. The layered material may be heated for at least about 6 hours, prior to cooling. In an aspect where the material layer and/or adhesive component are bonded in a separate step from the bonding of the polymer fibre layer, the material layer and/or adhesive component may be heated for at least about 1 hour, prior to cooling. The material layer and/or adhesive component may be heated for at least about 3 hours prior to cooling. The material layer and/or adhesive component may be heated for at least about 6 hours, prior to cooling.

In an aspect where the polymer fibre layer and/or adhesive component are bonded in a separate step from the bonding of the material layer, the polymer fibre layer and/or adhesive component may be heated for at least about 1 hour, prior to cooling. The polymer fibre layer and/or adhesive component may be heated for at least about 3 hours prior to cooling. The polymer fibre layer and/or adhesive component may be heated for at least about 6 hours, prior to cooling.

The adhesive component may be bonded to the material layer in a separate step/process than the bonding of the polymer fibre layer. The separate step/process may comprise the use of different heating times and/or temperatures.

The layered material may be cooled by standing at room temperature. The layered material may be cooled by refrigeration, or by application of a coolant.

Advantageously, during the heat treatment performed at, for example, around 80° C., adhesive material, such as PCL, melts (Tm=65° C.) whilst the material layer and/or the polymer fibre layer, such as PDO, remains intact (Tm=110° C.). This allows entrapment of the fibres from the layers into the adhesive layer, which acts as an adhesive upon solidification. Heat treatment may improve the mechanical properties of the patch, which results from an enhanced bonding of fibres, such as the PDO fibres.

Once formed, the scaffold may be impregnated, seeded or coated with an additional agent and/or cells.

The material layer may comprise or consist of a polymer. The material layer may be a woven polymer or a polymer fibre layer. The material layer may comprise a fibre, yarn, thread or monofilament.

The material layer may be provided by weaving a fibre, yarn, thread or monofilament into a weave, such as a plain weave. The weaving may be by a loom.

The fibre, yarn, thread or monofilament of the material layer may be formed by spinning. The fibre of the material layer and/or polymer fibre layer may be formed by spinning. The fibre of the adhesive component may be formed by spinning. The spinning may be electospinning. The material layer and/or the polymer fibre layer may be formed by electrospinning. The material layer and/or the polymer fibre layer may be formed by electrospinning under conditions which encourage alignment of the fibres, such as electrospinning on a rotating drum.

An additional agent may be incorporated into the material layer during the spinning process. An additional agent may be incorporated into the fibre of the polymer fibre layer during the spinning process. An additional agent may be incorporated into the fibre of the adhesive component during the spinning process.

The scaffold may be cut to size and/or shaped. The scaffold may be woven to the size needed. Frayed edges may be avoided by melting the edges, for example, by contacting the edges with a hot plate or cutting with a hot cutter or pen. The hot plate may be hotter than the melting temperature of the biodegradable scaffold, such as at least 150° C. Frayed edges may be avoided by embroidery or sewing at the edges of the scaffold.

The material layer, such as the material layer comprising PDO, may be treated with hexafluoro-2-propanol (HFIP), alkaline or plasma prior to bonding with the adhesive component. Where the material layer comprises PDO 7.0 or other PDO monofilament with larger fibre diameter (for example having a diameter greater than 100 µm), the material layer may be treated with hexafluoro-2-propanol (HFIP), alkaline or plasma prior to bonding with the adhesive component. Such treatment advantageously helps with the adhering process where one of the layers has smooth surface features, for example large diameter monofilaments.

The scaffold made by the method of the invention may maintain sufficient porosity and pore size for cell and protein capture, cell growth, and/or cell infiltration and migration. The biodegradable scaffold made by the method of the invention may remain sufficiently biocompatible.

According to another aspect of the invention, there is provided the use of PCL for adhering a material layer to a polymer fibre layer; wherein the PCL has a lower melting temperature (Tm) than the material layer and the polymer fibre layer.

According to another aspect of the invention, there is provided the use of PCL for adhering two or more layers of electrospun polymer layers together, wherein the PCL has a lower melting temperature (Tm) than the two or more electrospun polymer layers.

According to another aspect of the invention, there is provided a scaffold patch comprising the scaffold in accordance with the invention herein.

The scaffold patch may be suitable for tissue repair in a mammalian subject. The scaffold patch may be biocompatible. The scaffold patch may be a wound dressing or plaster.

Where the use of the scaffold and/or scaffold patch is for wound dressing, the material layer may comprise or consists of polymer fibre layer.

The skilled person will understand that optional features of one embodiment or aspect of the invention may be applicable, where appropriate, to other embodiments or aspects of the invention.

A BRIEF DESCRIPTION OF THE DRAWINGS

Embodiments of the invention will now be described in more detail, by way of example only, with reference to the accompanying drawings.

FIG. 1A-1I—illustrates a method of creating multi-layered scaffolds from electrospun and non-electrospun mats according to the invention and depicts the architecture of the prototype layered electrospun/woven scaffold (FIG. 1I). Conventional electrospun mats are flat, fine sheets and their application as tissue scaffolds is usually limited by inadequate thickness (as a result of the spinning technique) and low strength. This invention introduces a simple, non-destructive technique to stack and bond electrospun and non-electrospun layers using a thermoplastic mat (FIG. 1A). The thermoplastic mat is used to bond the layers to each other in a stable manner, and as it is electrospun, the porosity at the interface between the layers can be controlled. Resulting constructs can be adjusted to have the appropriate thickness, texture and tensile properties depending on the application. For example, FIG. 1B and FIG. 1C are scanning electron micrographs of different prototypes that can be assembled using this method: (FIG. 1B), multi-layered electrospun sheets; and (FIG. 1C), a woven polydioxanone textile sandwiched between two electrospun mats. In this study, a specific scaffold for rotator cuff augmentation was designed and tested. (FIG. 1D) is a schematic diagram of the prototype scaffold; (FIG. 1E) is a cross-sectional view of the scaffold; (FIG. 1F), the woven layer; (FIG. 1G), the random electrospun PCL thermoplastic adhesive layer; (FIG. 1H), aligned PDO electrospun mat, the tendon-facing layer of the scaffold, collected on a drum rotating at 2000 rpm. Unless specified scale bars are 100 μm.

Figure 2:
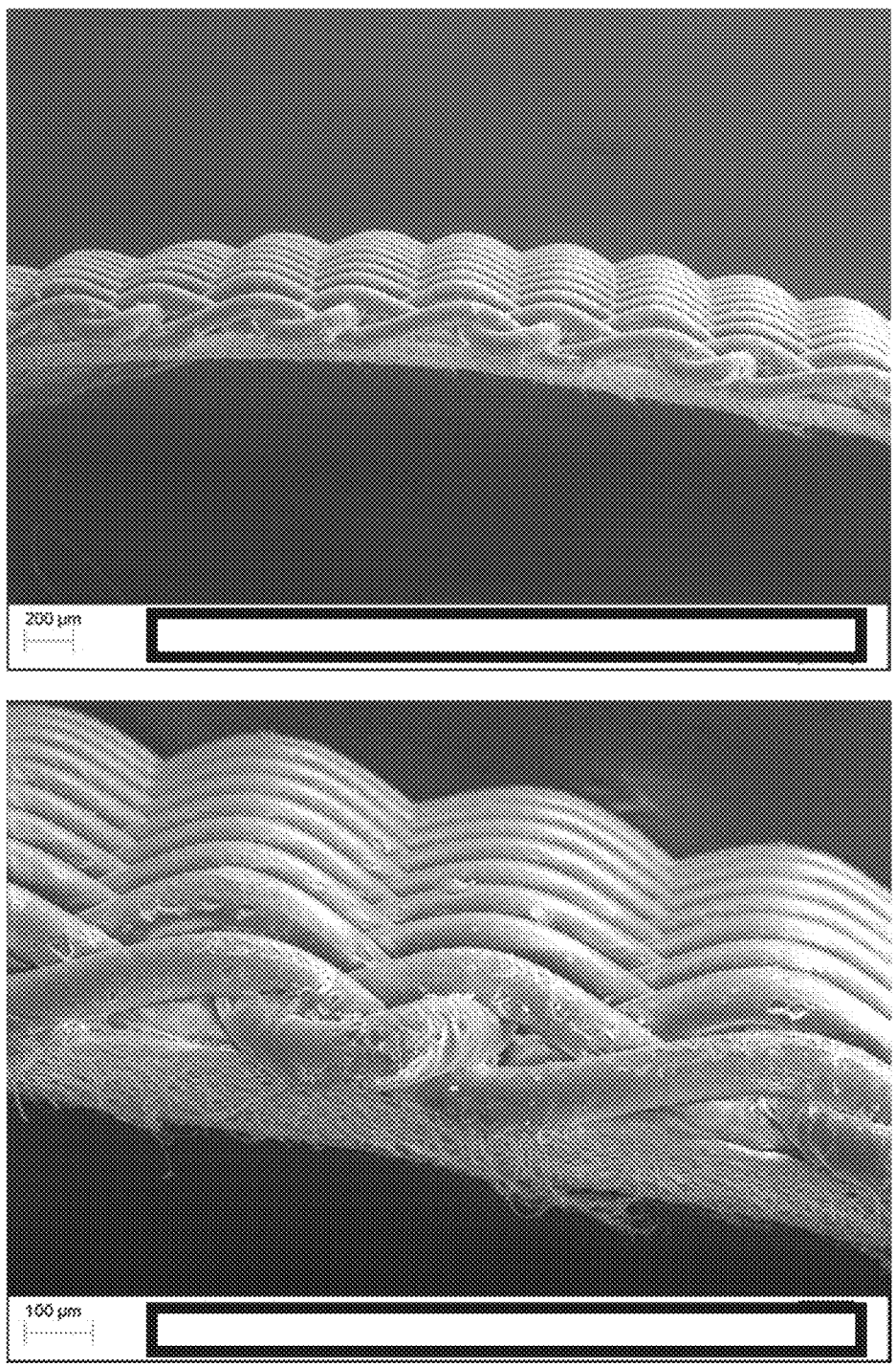

FIG. 2—SEM images showing the assembled construction, with the woven monofilament layer well adhered to the nanofibrillar electrospun component using the PCL as a heat-responsive glue.

Figure 3:
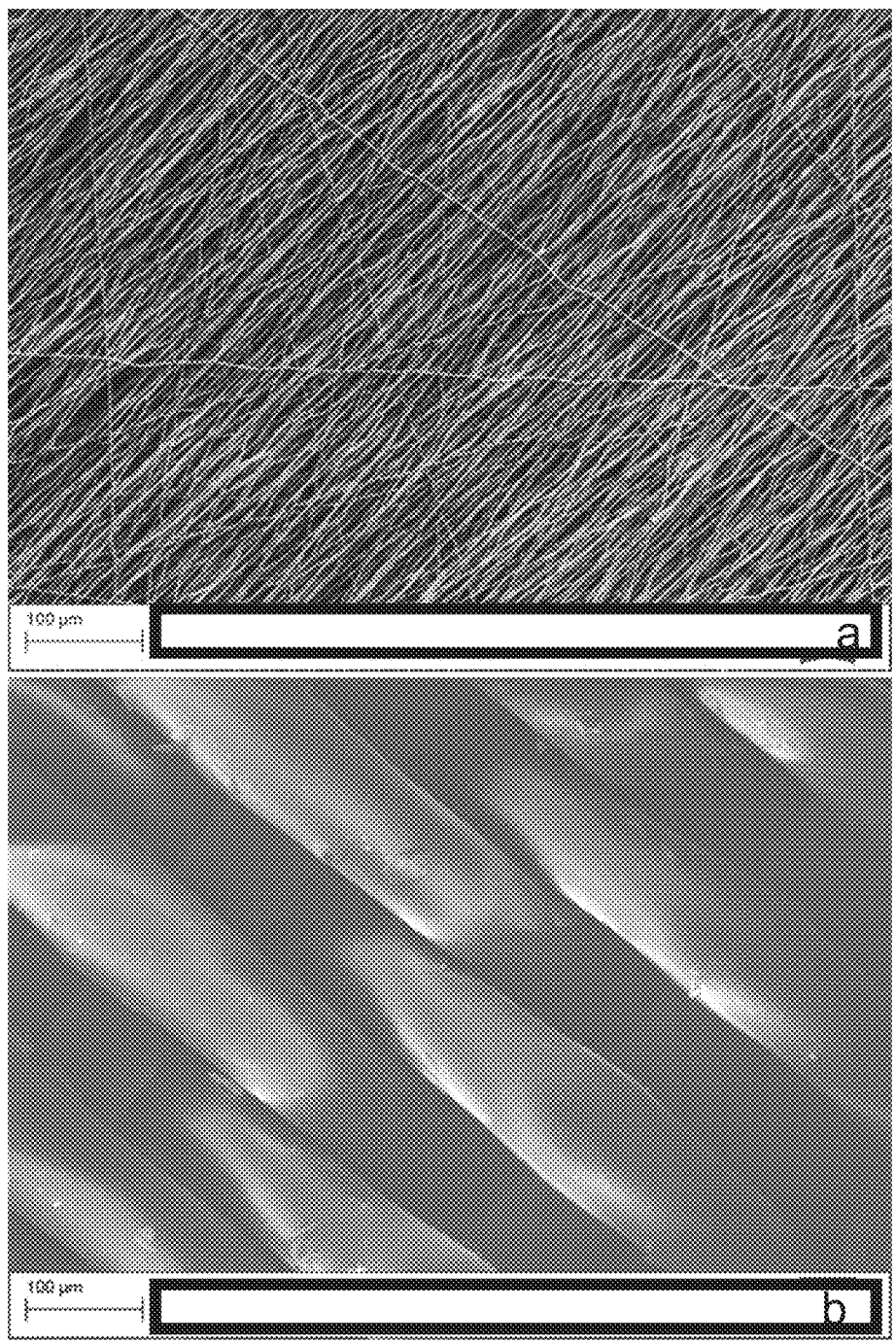

FIG. 3—SEM images showing the gross appearance of the electrospun PDO layer component (a) and woven PDO monofilament component (B) of the patch prior to assembly.

Figure 4:
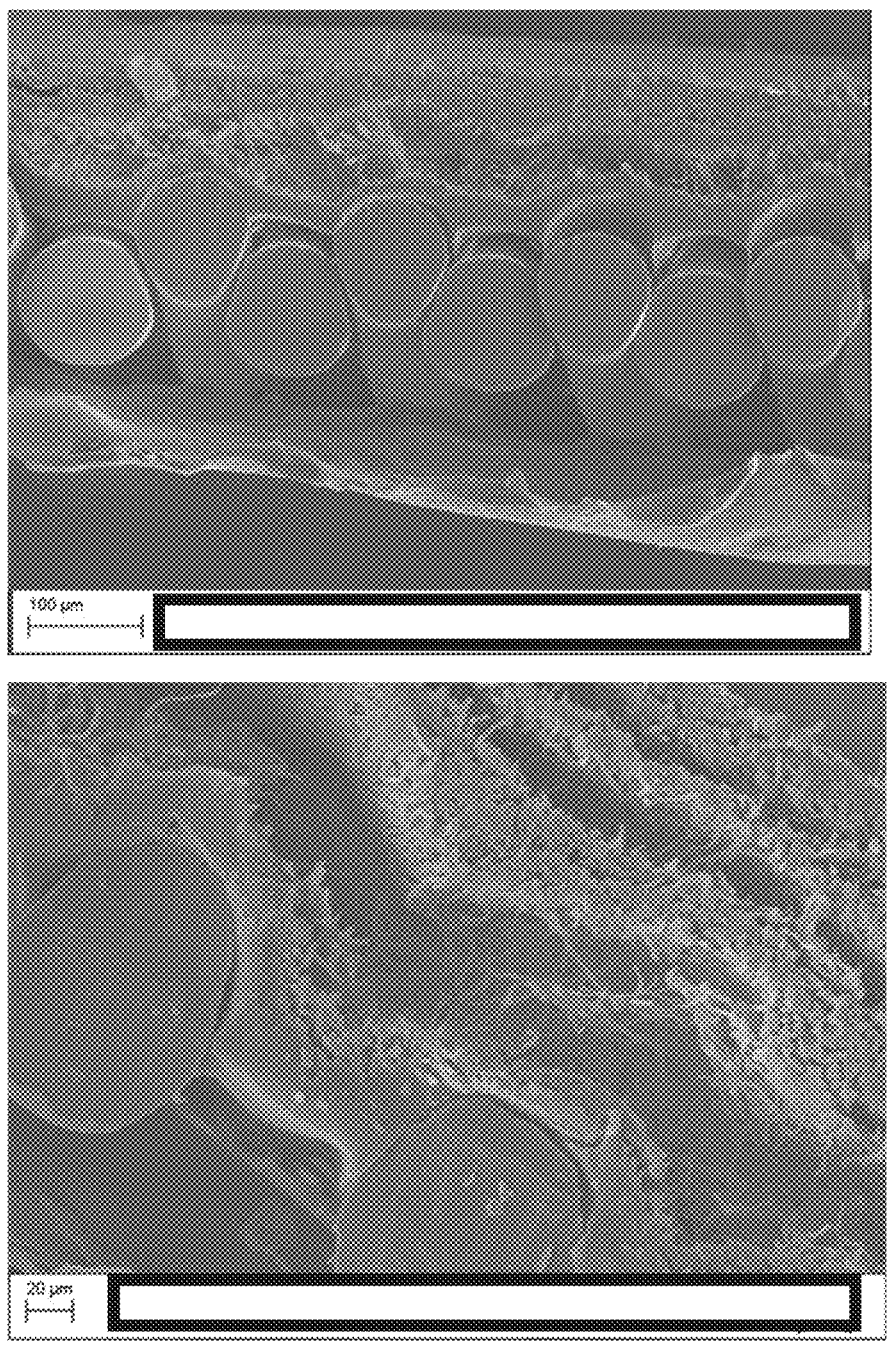

FIG. 4—shows a transversal cut through assembled layered components.

Figures 5A, 5B, 5C, 5D, 5E, 5F, 5G, 5H:
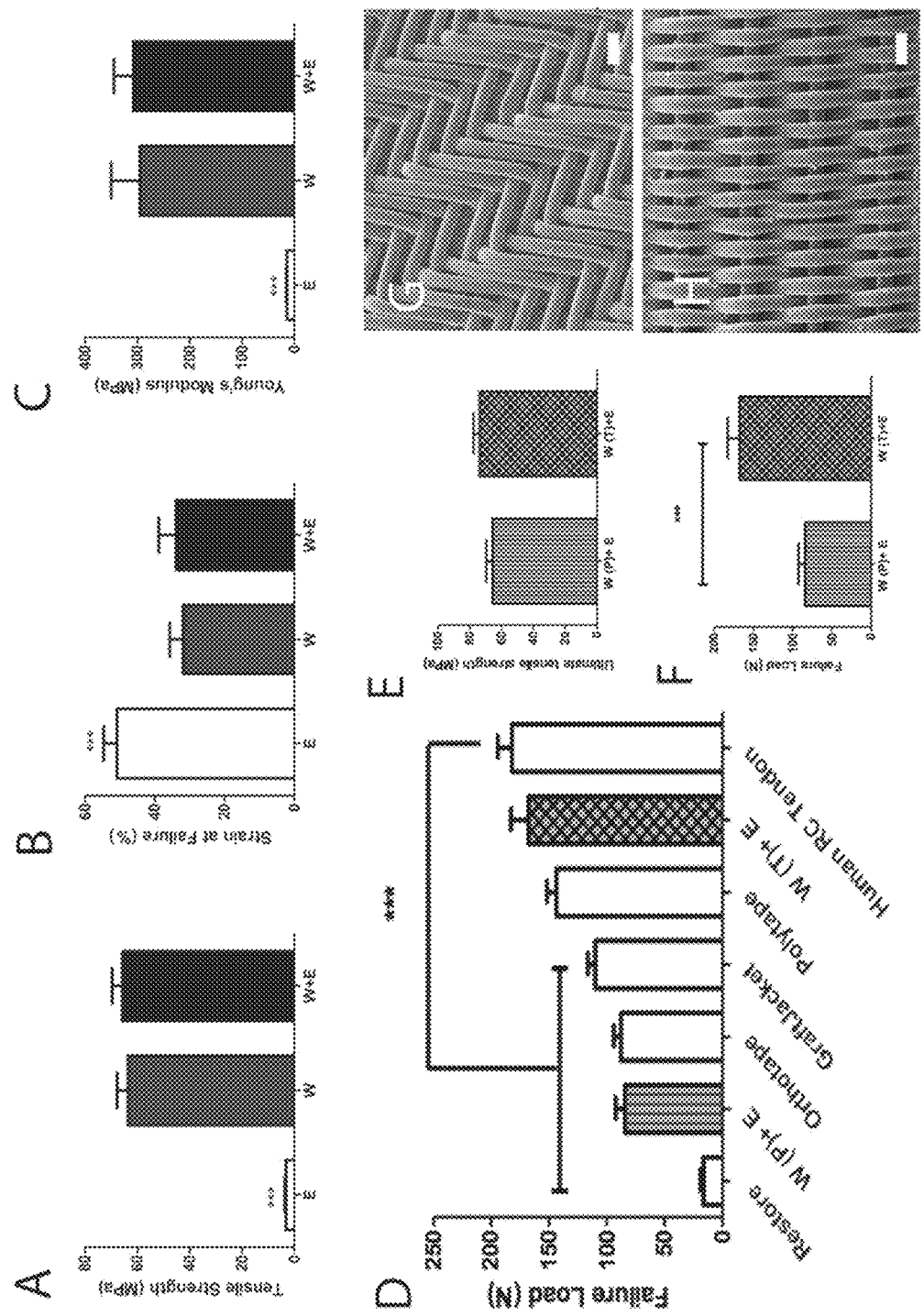

FIG. 5A-5H—demonstrates that layered woven and electrospun scaffolds can be adjusted to yield mechanical properties similar to native tendon. The mechanical properties of the woven layer were preserved following the bonding with the electrospun layer, and by varying weave patterns suture pull out could be enhanced. FIGS. 5A, 5B and 5C, Tensile strength (MPa), strain to failure (%) and Young's modulus (MPa) of the electrospun layer (FIG. 5E), woven layer (W) and assembled scaffold (W+E); FIG. 5D, suture retention properties of the two variations of the layered scaffold (plain or twill) in comparison to a selection of available commercial patches (Restore, Orthotape, Graft Jacket and Polytape) and human rotator cuff tendon; FIG. 5E, FIG. 5F, ultimate tensile strength (MPa) and suture failure load (N) of plain and twill weave; FIG. 5G, scanning electron micrographs of the twill weave [W(T)]; FIG. 5H, scanning electron micrographs of the plain weave [W(P)]; Scale bars are 200 μm.

Figure 6:
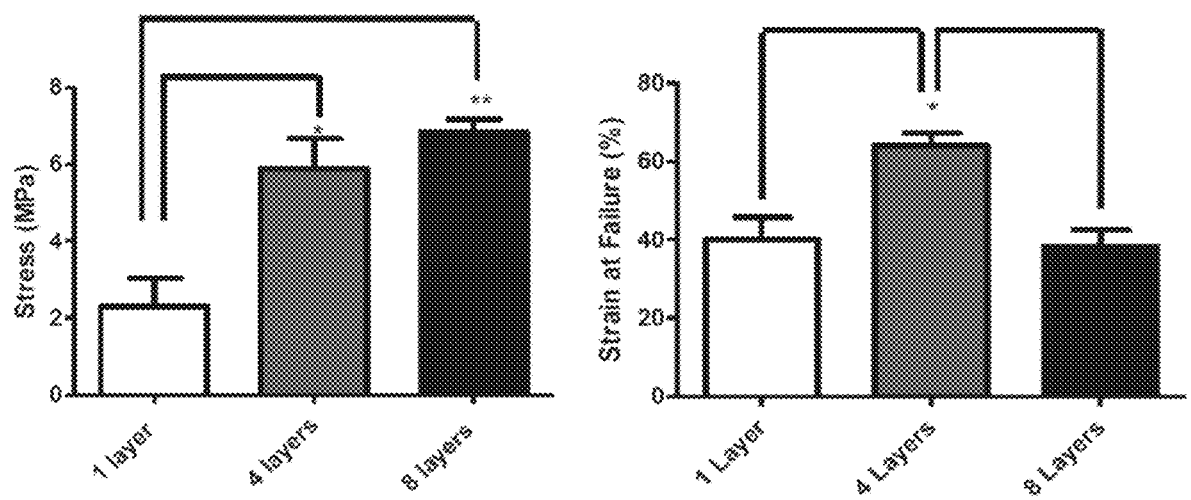

FIG. 6—illustrates the tensile strength and strain at failure % of a single electrospun layer and an assembly of 4 and 8 layers of the same material.

Figure 7:
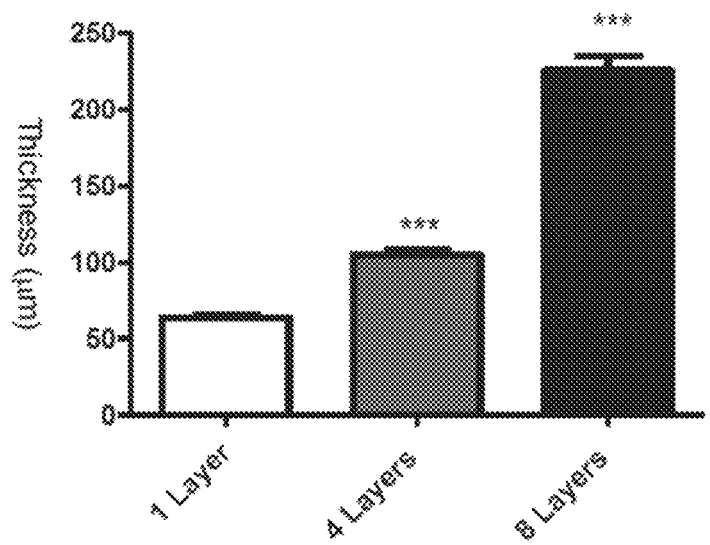

FIG. 7—shows a comparison between thickness of a single electrospun layer and an assembly of 4 and 8 layers of the same material.

Figure 8:
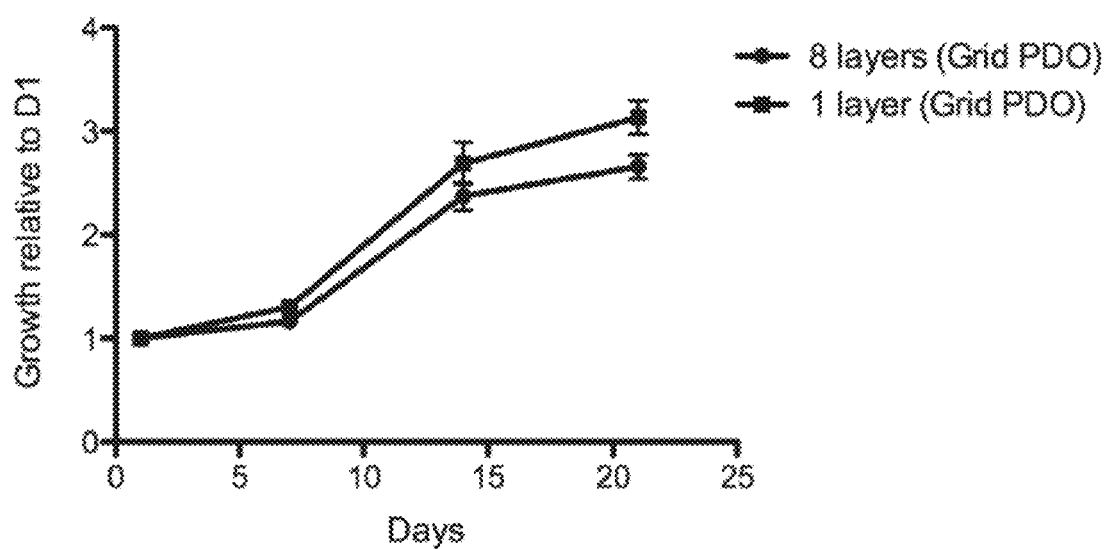

FIG. 8—shows growth of tendon derived cells on single and multilayered PDO scaffolds over 21 days, measured using AB (n=3). There was no significance difference in cell growth (relative to day 1) between multilayer and single electropsun layer constructions.

Figure 9:
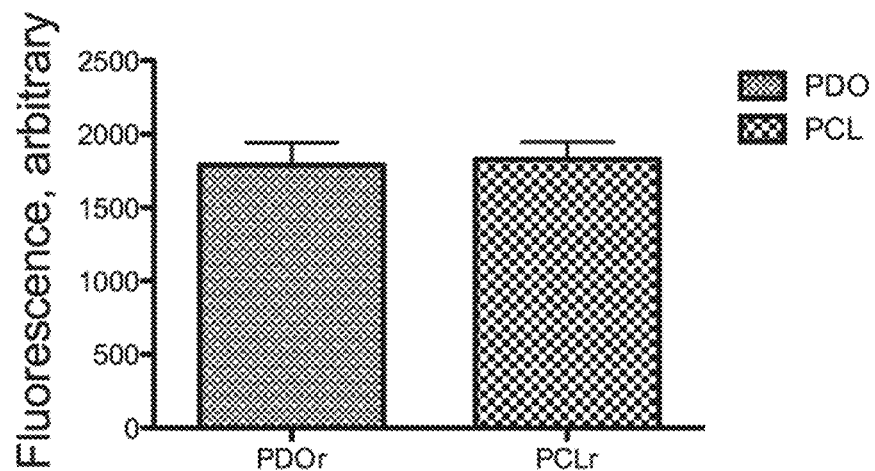

FIG. 9—compares adhesion of tendon derived cells to a single layer of electrospun PDO and PCL and reveals that there were no statistical differences in viable cells attached to these materials 24 hours after seeding. Adhesion was monitored using AlamarBlue.

Figure 10:
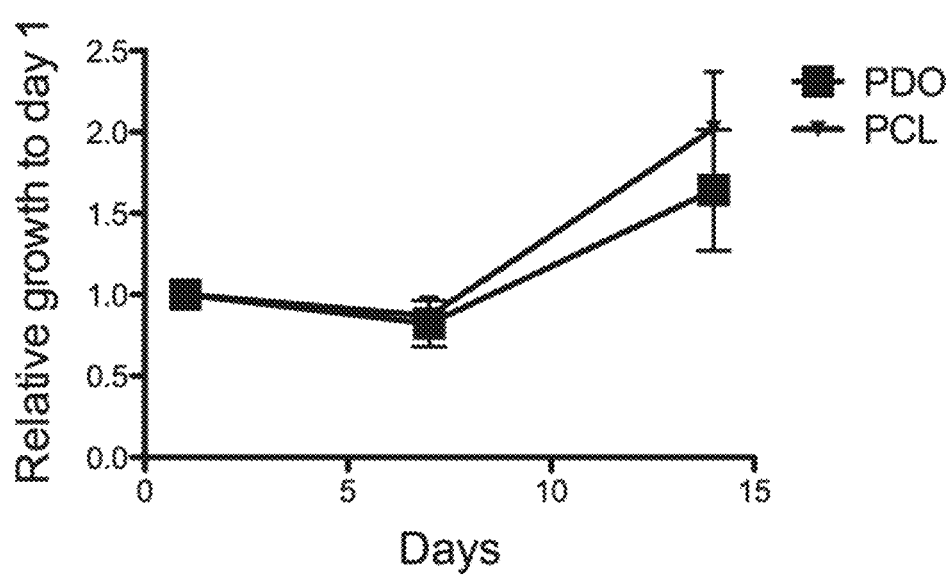

FIG. 10—shows growth of tendon derived cells on a single layer of electrospun PCL and PDO scaffolds over 14 days, measured using AB (n=4). There was no statistical difference in cell growth (relative to day 1) between these two materials.

Figure 11:
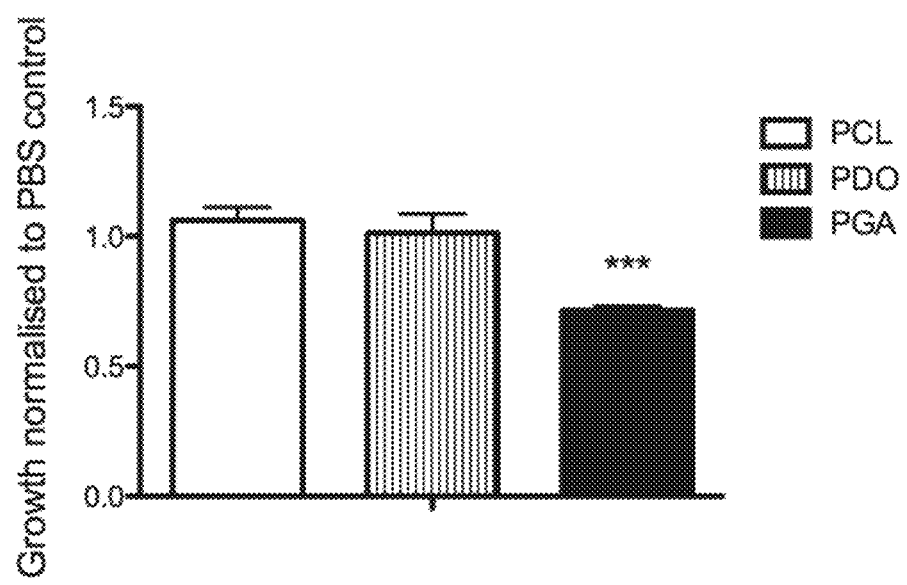

FIG. 11—cells exposed to phosphate buffered saline conditioned with electrospun PCL, PDO and PGA showed differential responses to these materials. Whilst PGA-exposed cells showed reduced cell growth compared to PBS control, there was no growth inhibition in cells exposed to PCL and PDO conditioned PBS. PBS was conditioned for 1 month and cells were exposed to a maximum of 0.5 mg/ml material.

Figures 12A, 12B, 12C, 12D, 12E, 12F, 12G:
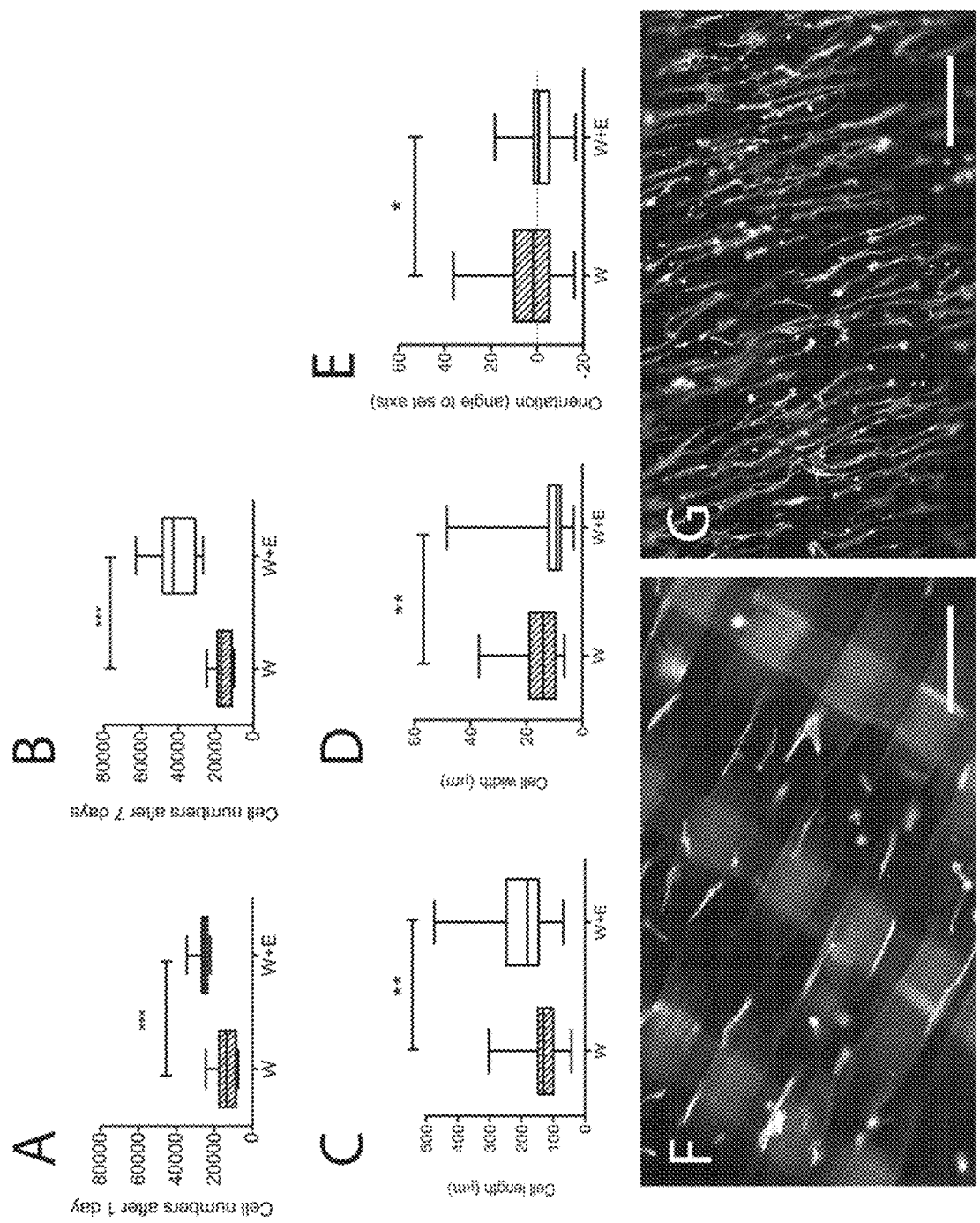

FIG. 12A-12G—demonstrates that the addition of the aligned electrospun layer enhances cell attachment and growth and modulates cell shape and orientation. Human primary tendon-derived cells from torn rotator cuffs were seeded on the woven component alone (W) and on the layered scaffold (W+E). Boxes and whiskers are mean and min-to-max, respectively. a, b, A statistically significant larger number of viable tendon-derived cells were attached to the layered scaffold on day 1 (FIG. 12A) and 7 (FIG. 12B), measured using alamarBlue metabolic assay (n=8); FIG. 12C-12E, cells grown on the layered scaffold had a longer (FIG. 12C), narrower shape (FIG. 12D) and a more directional orientation to the axis of the patch (axis set as 0, FIG. 12E) compared with cells grown on the woven component. Fluorescence images of cells grown on the scaffolds for 3 days illustrate the higher cell density and differential morphology on the electrospun surface (FIG. 12G) compared to the woven component (FIG. 12F). Cells were fluorescently labelled for actin, scale bar 200 μm. (*p<0.05, p<0.01, *p<0.001).

Figures 13A, 13B, 13C:
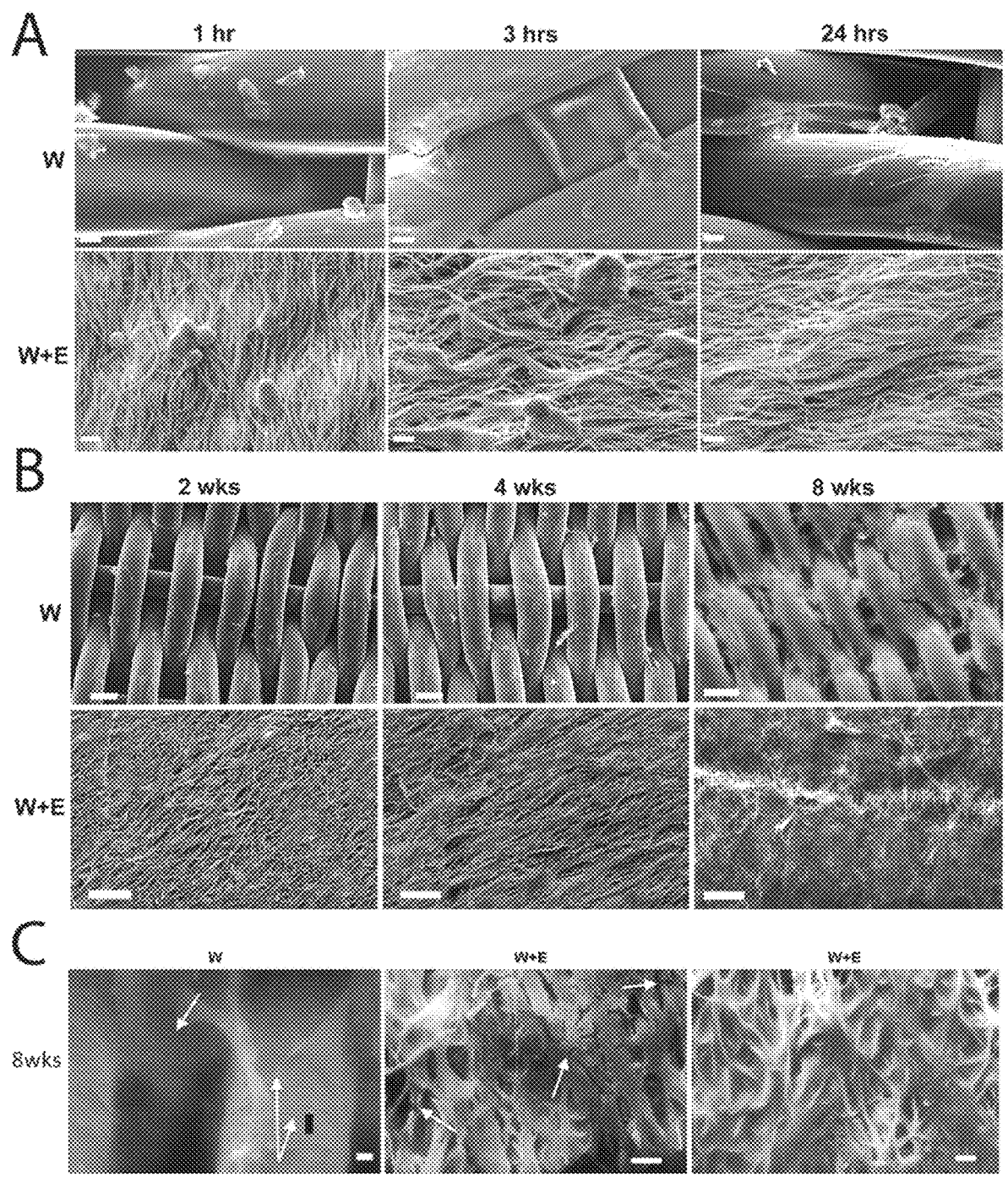

FIG. 13A-13C—demonstrates that the addition of the aligned electrospun layer accelerates cell attachment and enhances the formation of an interconnected monolayer. Scanning electron micrographs show the appearance of tendon derived cells grown on the layered scaffold (W+E) and the woven component (W) at different time points. FIG. 13A, Micrographs of the first 24 hours after cell seeding, showing cells flattening and extending within 3 hours on the layered scaffold compared to the woven component. Scale bars are 10 μm; FIG. 13B, micrographs of the scaffolds after 2, 4 and 8 week of culture, showing a gradual increase in cell coverage and the formation of a monolayer on both layered scaffold and the woven component, with a denser and better-interconnected cell population on the layered scaffold. Scale bars are 100 μm. The aligned/crimped nanofibres of the layered scaffold, visible at 2 and 4 weeks, are not visible by week 8, when cells appear to be deeply embedded in a fibrous matrix; FIG. 13C, Higher magnification micrographs of the layered scaffold at week 8 showing the PDO to be partly degraded. The arrows indicate cracks in the extruded monofilaments of the weave and breakages of the nanofibres in the electrospun component, which appear embedded in a dense matrix. Scale bars are 10 μm.

Figures 14A, 14O:
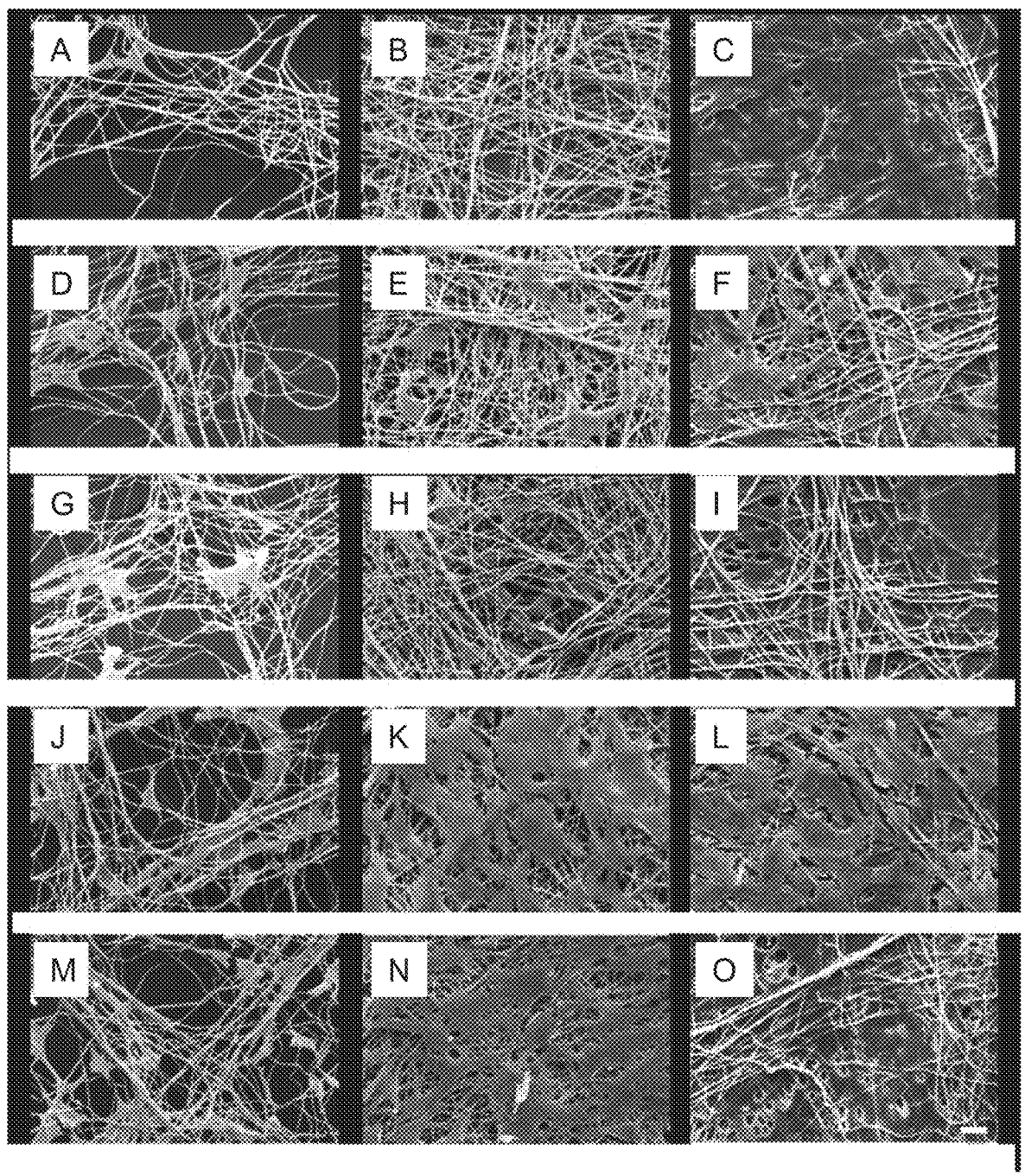

FIG. 14A-14O—SEM images showing that, by controlling the thickness of the binding layer (PCL), the migration of tenocytes through the construct can be allowed or prevented. The study compares a single electrospun grid layer (left column, images FIG. 14A, FIG. 14D, FIG. 14G, FIG. 14J and FIG. 14M), a construct made of 4 layers of electrospun grid with a thin layer of the binding component electrospun PCL (middle column, images FIG. 14B, FIG. 14E, FIG. 14H, FIG. 14K and FIG. 14N) and a construct made of 4 layers of electrospun grid with a thick binding layer of electrspun PCL (right column, images FIG. 14C, FIG. 14F, FIG. 14I, FIG. 14L and FIG. 14O). FIG. 14A-14C: initial scaffolds (no cells); FIG. 14D-14F: 7 days of culture, upper side; FIG. 14G-14I: 7 days of culture, lower side; FIG. 14J-14L: 14 days of culture, upper side; FIG. 14M-14O: 14 days of culture, lower side. Scale bar: 20 μm. As can be seen in images J/N, binding 4 layers with a thin PCL layer enabled cells migration, and they covered both sides of the scaffolds. Images L/O show that very few cells managed to migrate through a scaffold of 4 layers with a thick binding PCL layer. Thus, varying the thickness/density of the binding layer could be used to control cell migration.

Figure 15:
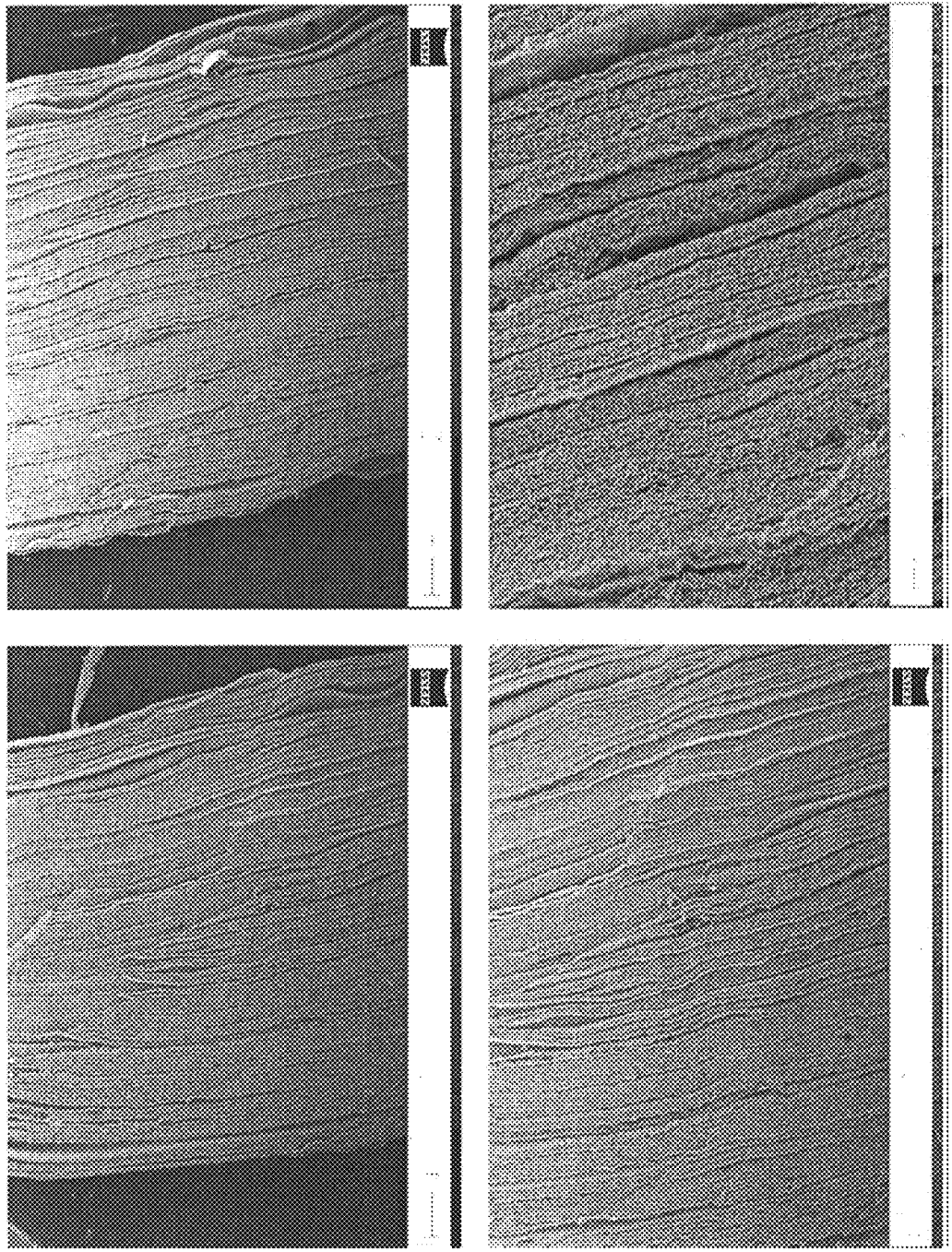
Figures 16A, 16B, 16C, 16D, 16E, 16F, 16G, 16H:
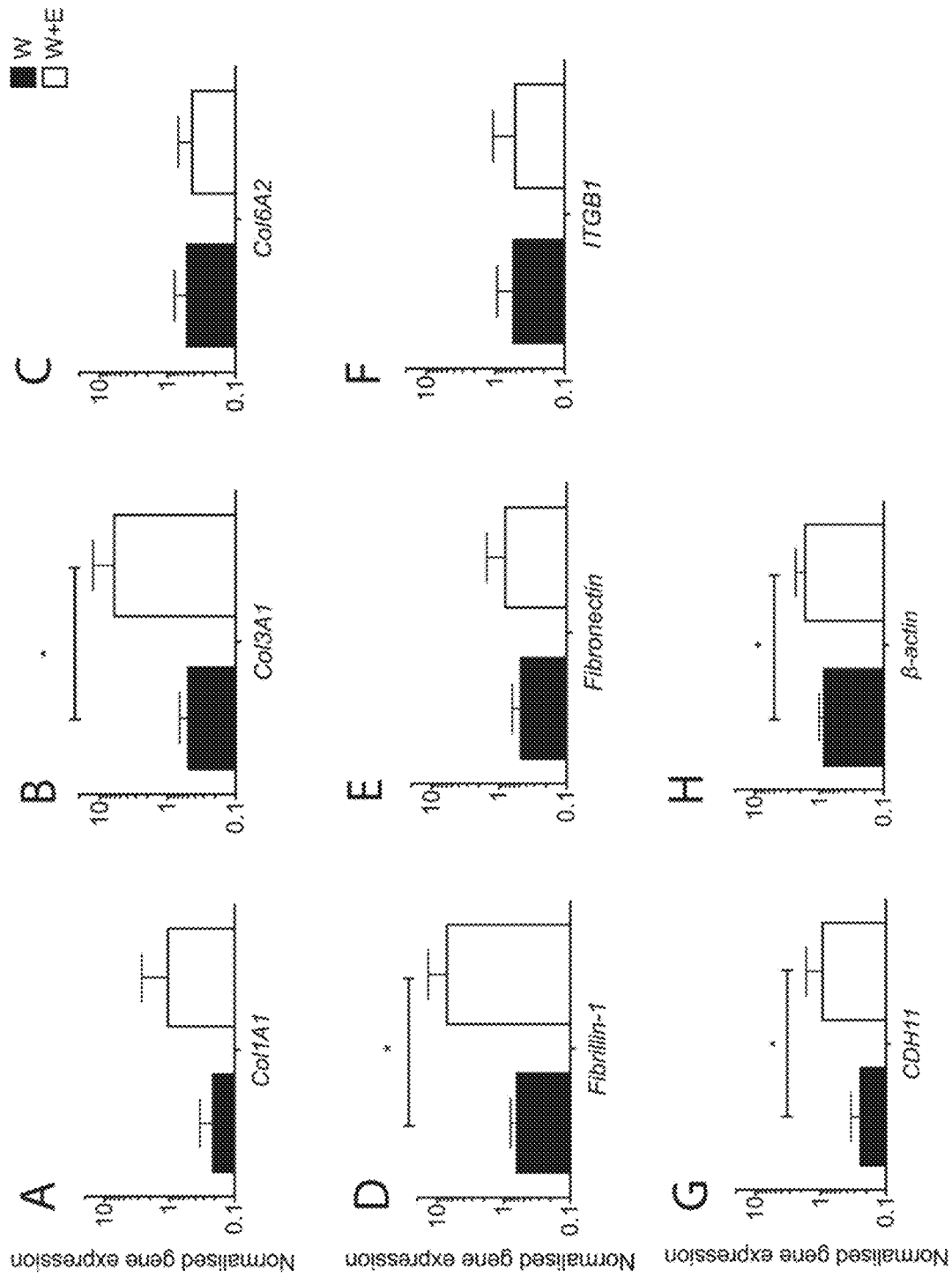

FIG. 15—shows a series of transverse cut views of another example of the invention in different magnifications. The scaffold comprises multiple non-woven electrospun polymer layers (such as the one shown in FIG. 3a) held together by the adhesive component PCL. This demonstrates that using the reported technique, it is possible to stack up the fine electrospun layers until a forming a scaffold of a significant volume. Such a construction could be used when more bulky scaffolds are needed, for example to fill cartilage legions.

FIG. 16A-16H—the addition of the aligned electrospun layer enhanced relative gene expression of tendon markers. Analysis of collagen I (Col1A1), collagen III (Col3A1), collagen VI (Col6A2), fibrillin 1 (FBN1), fibronectin (FN1), integrin β1 (ITGB1), cadherin 11 (CDH11) and β-actin (ACTB) after 7 days of culture on the layered scaffold (W+E) or the woven component only (W). Gene expression was normalised to GAPDH and to plastic control (ΔΔCT). Cells grown on the layered scaffold had a significantly increased collagen III expression (FIG. 16B), typically associated with early phase tendon regeneration. Fibrillin-1, associated with elastic fibre formation, was also upregulated (FIG. 16D), as well as the cytoskeletal fibrous protein β-actin (FIG. 16H) and cadherin 11 (FIG. 16G), suggesting increased cell-cell contacts. There was no significant effect on fibronectin (FIG. 16E) or integrin β1 expression (FIG. 16F), the latter being associated with fibronectin binding (n=6 patches; *p<0.05).

FIG. 17A-17G—illustrates that the layered scaffold of the invention was well integrated in an in vivo rat model. FIG. 17A, An illustration of the scaffold placement in the rat shoulder. An incision was made at the distal end of the spine of the scapula, the infraspinatus was exposed and transected, and the layered scaffold used as a repair over the defect. FIG. 17B-17E, scanning electron micrographs showing tissue ingrowth into the layered scaffold after (FIG. 17B) 2 weeks, after (FIG. 17C) 4 weeks, (FIG. 17D) 6 weeks and (FIG. 17E) 12 weeks; FIG. 17F, capsule size increased up to 2 weeks in vivo, after which it was reduced and better-defined over 12 weeks. (FIG. 17G) failure load of the layered scaffold ex-vivo showing a significant reduction to 2 weeks but an increase in mechanical strength by 8 weeks (measured failure load is lower than in FIG. 5 because plain weave was used, as well as reduced dimensions to fit the rat's shoulder).

Figures 18A, 18B, 18C, 18D:
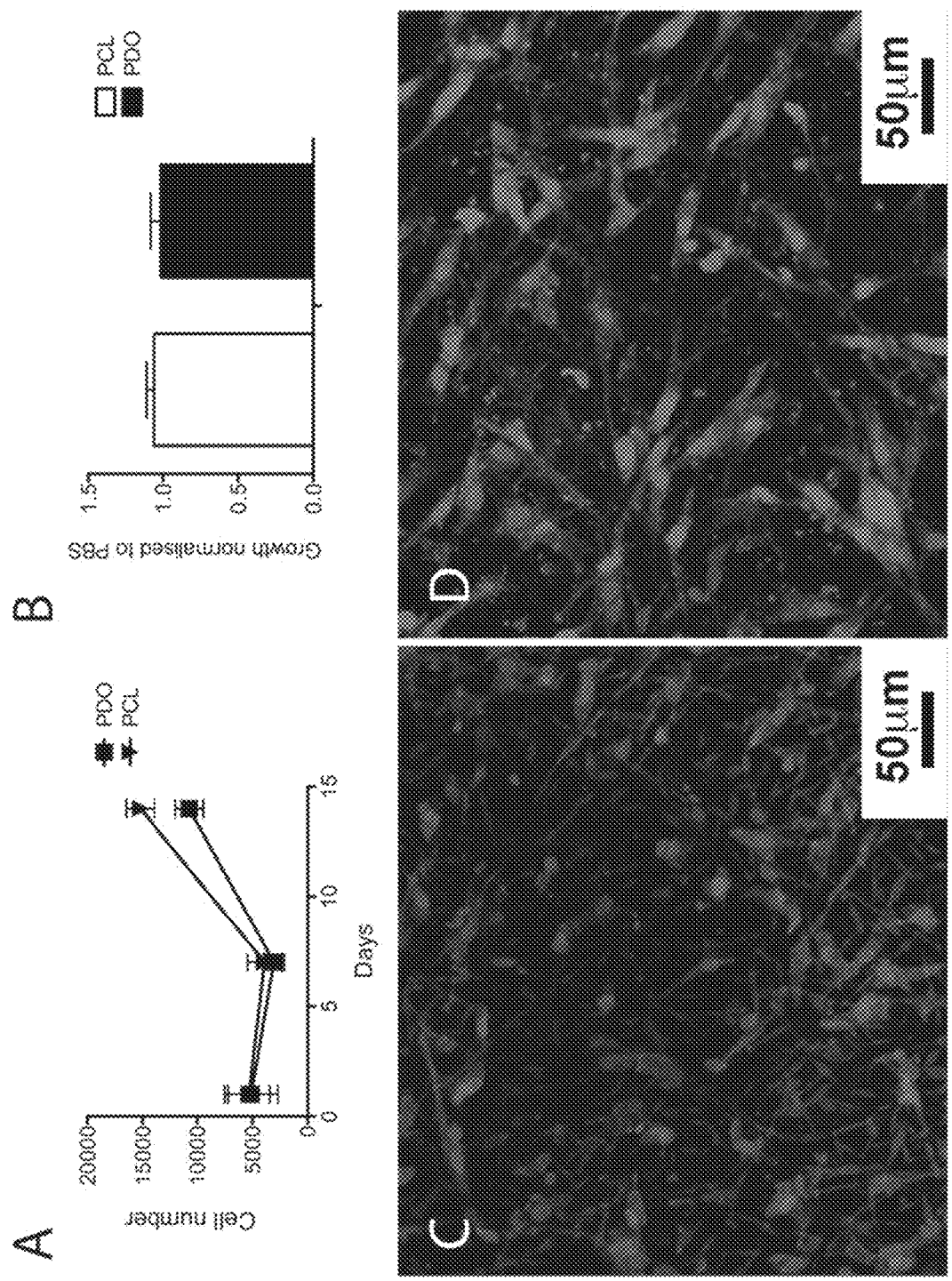

FIG. 18A-18D—PDO and PCL show equivalent tendon cell response in vitro. The combination of the two degradable polymers, PDO and PCL, in the layered scaffold required a comparative evaluation of cell response. Whilst initially, cells are attached to the PDO mat, but within 4-6 weeks, the degradation of the PDO will expose the thermoplastic bonding layer (PCL). Random electrospun mats of PDO and PCL were used for the comparative study. Cell adhesion, growth, spreading, morphology and response to conditioned media were equivalent for the two polymers in a random, electrospun form. FIG. 18A, tendon cell numbers on the mats over 14 days, measured using alamarBlue metabolic assay (n=4); FIG. 18B, cells growth in conditioned media (n=3); FIG. 18C-18D, cells fluorescently labelled for actin (red), counterstained for nuclear DNA (blue) and imaged by confocal microscopy, showing grossly similar elongation and spreading on PDO (FIG. 18C) and PCL (FIG. 18D). Note that PDO, but not PCL scaffolds, showed autofluorescence at the UV range, making the electrospun fibres visible in blue.

Figure 19:
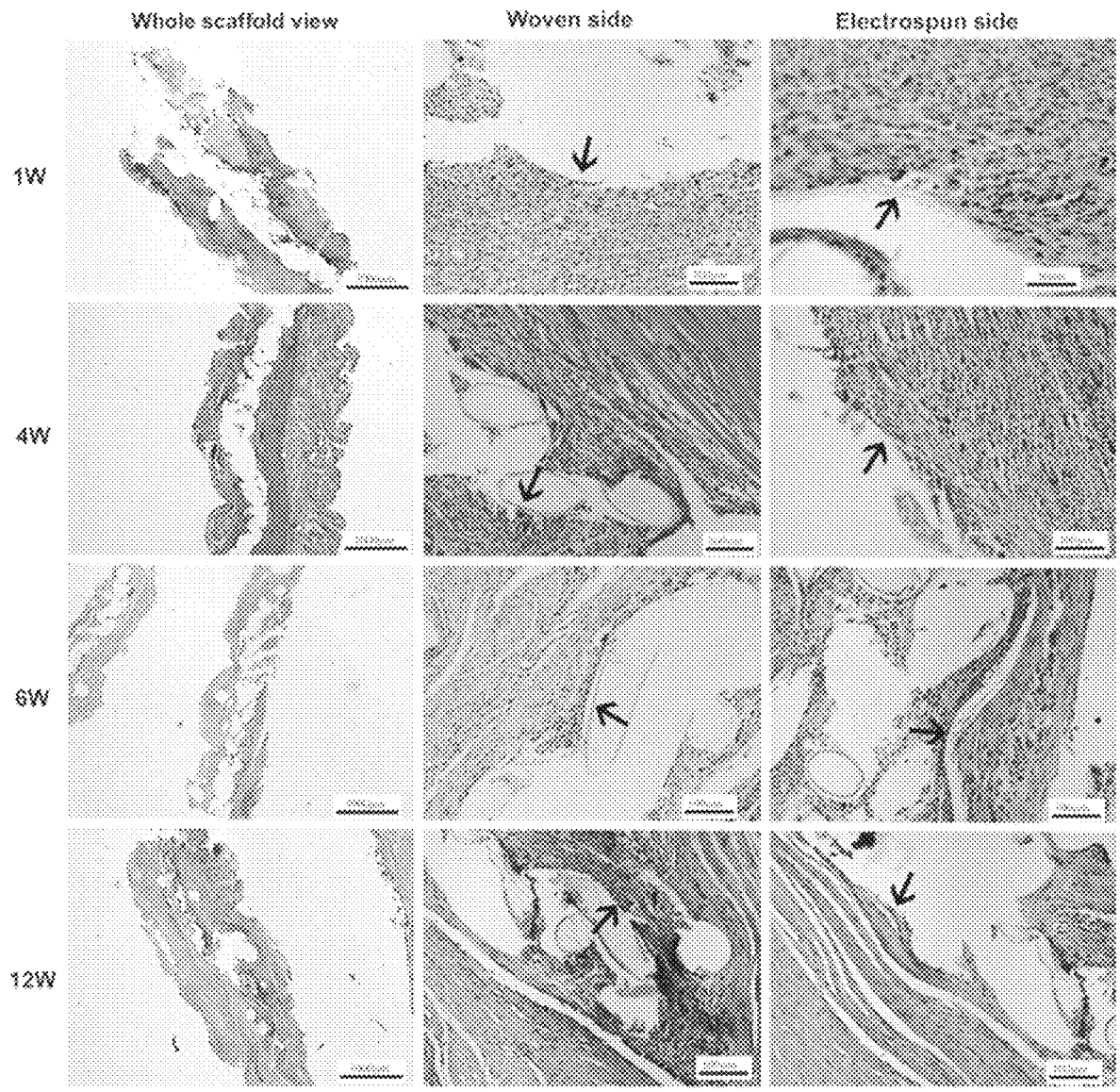

FIG. 19—illustrates the implantation of the layered scaffold in a rat model. Hematoxylin-eosin stained sections showed gradual cell infiltration of the electrospun component over 12 weeks. Whole views of the patch showed increased integration of the layered scaffold over time, with fibres surrounded by dense tissue by week 12. The electrospun side of the scaffold was infiltrated by cells which appeared arranged in oriented arrays within bundles of pale fibres. The electrospun material was most clearly visible on week 1. The relatively organized tissue around the electrospun layer appeared thicker and more pronounced after 4 weeks, although it was harder to distinguish any pale electrospun-like fibres at this time point. At the 6 and 12 week there were still clear arrays of well-oriented cells in the vicinity of the scaffold. FBGCs were most visible at week 4 on the electrospun side of the scaffold, and there was a clear reduction in their numbers thereafter.

Figure 20:
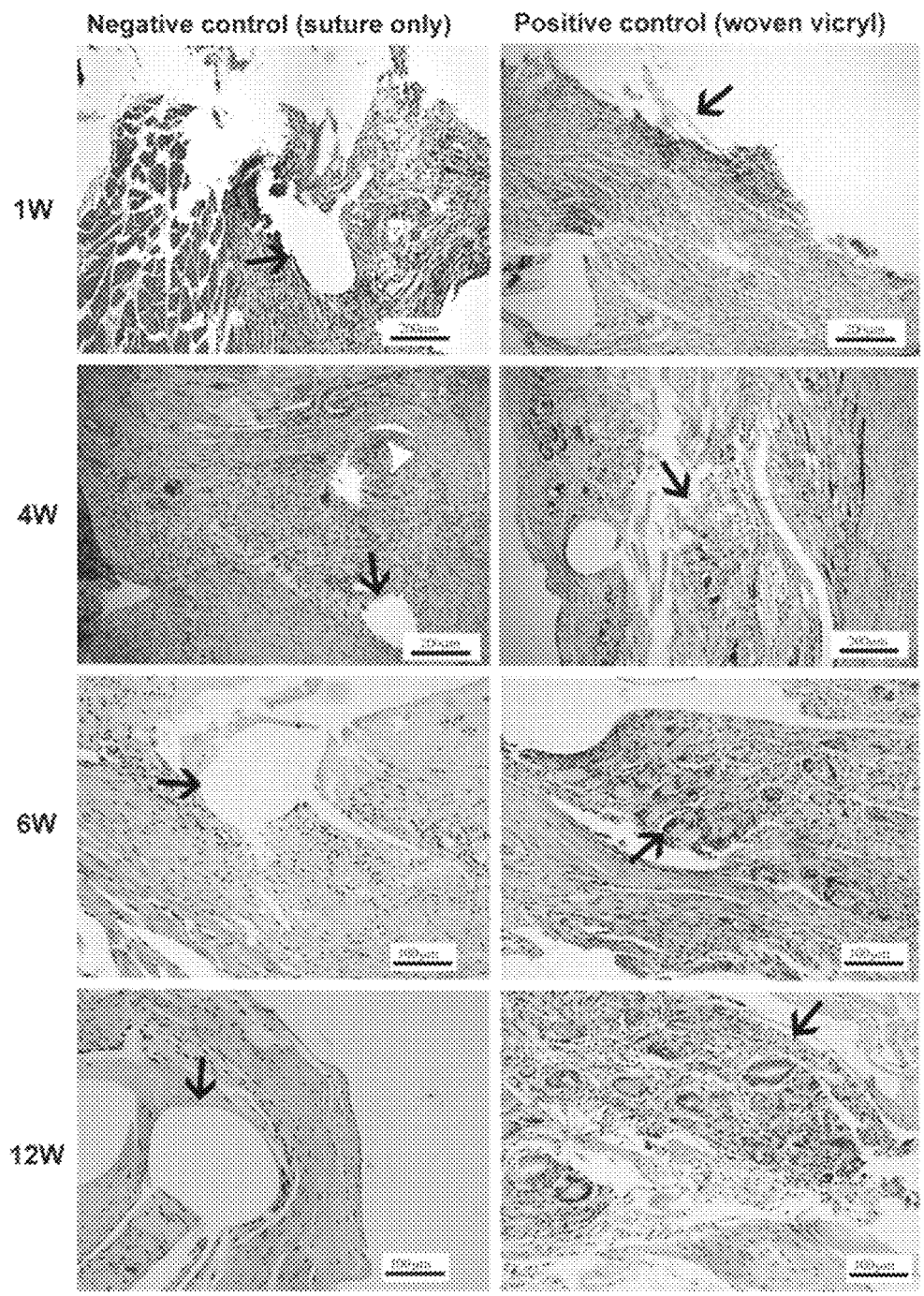
Figures 21A, 21B, 21C, 21D, 21E, 21F:
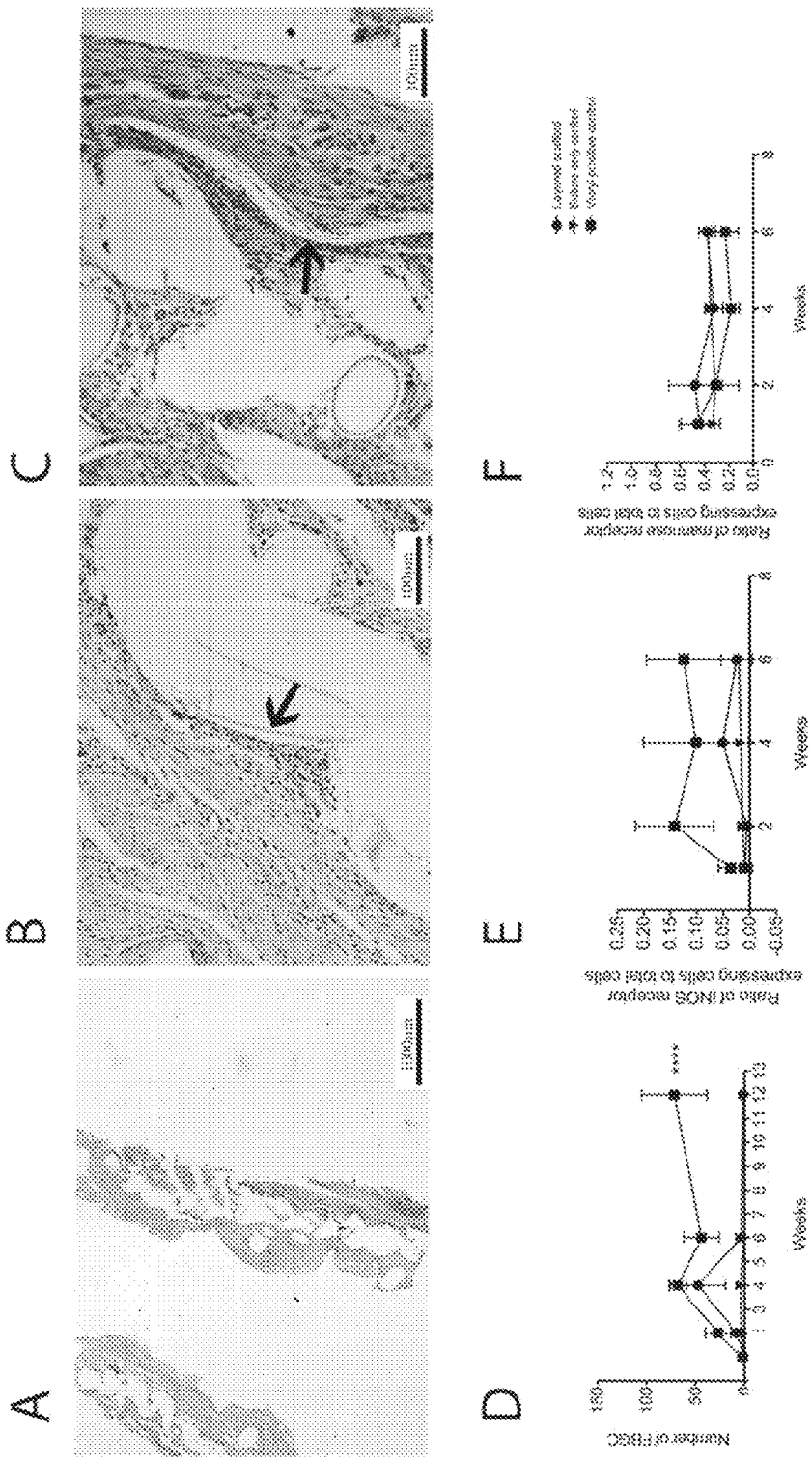

FIG. 20—illustrates controls used in the rat model. A prolene suture repair (suture only) was used as a negative control for immune response a vicryl weave was used as a positive control. From 4 weeks onward, the woven vicryl patch was surrounded by a large number of foreign body giant cells, and this was maintained up to 12 weeks. Little or no FBGC were seen in the suture-only control.

FIG. 21A-21F—the layered scaffold showed an excellent tissue reaction in an in vivo rat model in terms of foreign body giant cells (FBGC) and macrophage subtypes. (FIG. 21A) Hematoxylin-eosin stained section showing a whole view of the integrated scaffold after 6 weeks in vivo. (FIG. 21B) after 6 weeks, the tissue surrounding the woven side of the scaffold shows high cellularity and little or no FBGCs, (FIG. 21C) after 6 weeks, the electrospun component appears engulfed by cellular, well-aligned tissue (FIG. 21D) Numbers of FBGC around the scaffold increased up to 4 weeks but returned to levels comparable to the negative control (suture only) thereafter. Woven Vicryl (polygalactin 910) was used as positive control, as it induced a more persistent foreign body response over 12 weeks. (FIG. 21E), (FIG. 21F), Ratios of macrophage subtype 1 and 2 in the tissue surrounding the scaffold over time. There was little or no difference between the layered scaffold and the negative control (suture only). Macrophages were stained using iNOS for subtype M1 (FIG. 21E) and mannose receptor for subtype M2 (F). **$p<0.0001$. $p<0.01$, ****$p<0.0001$.

Figure 22:
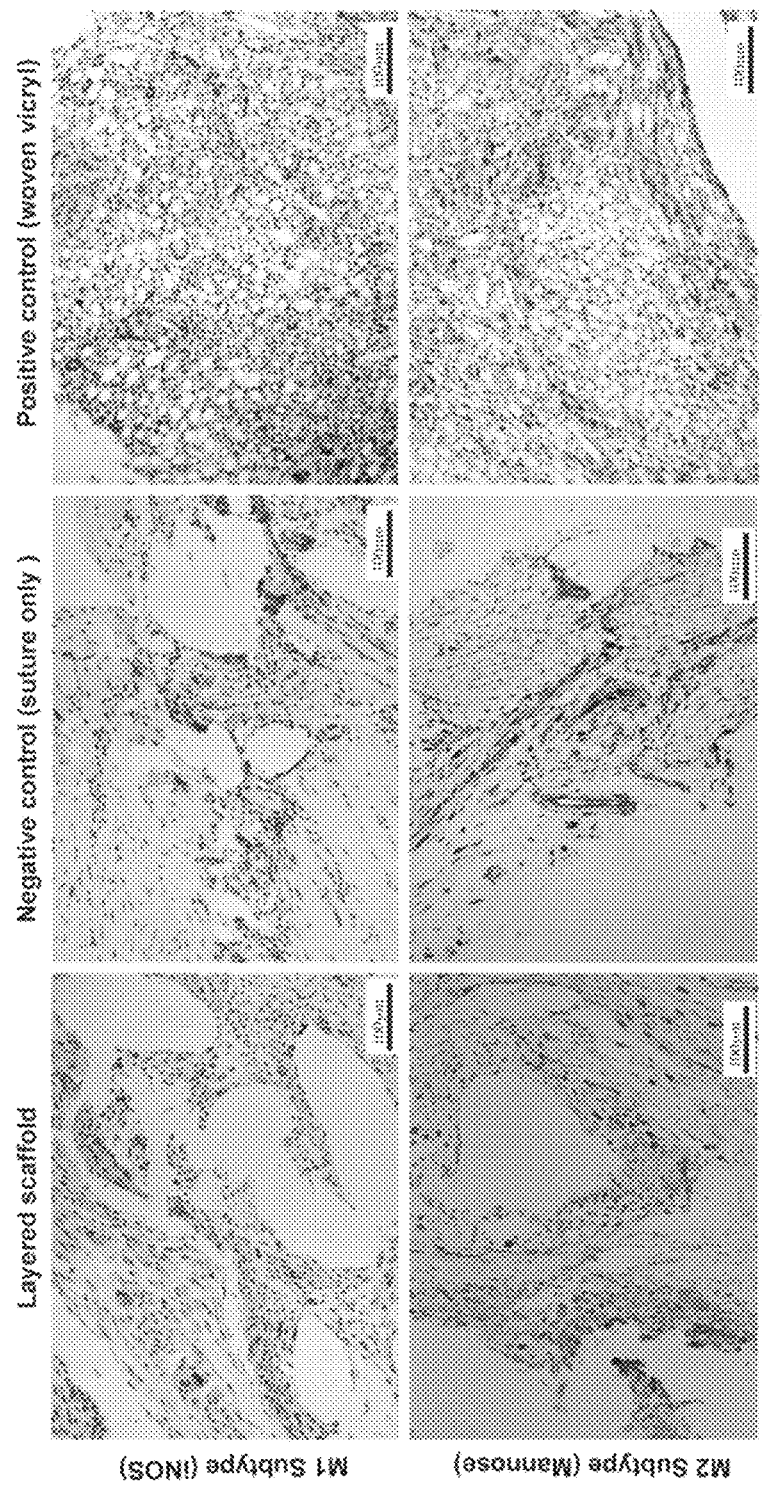

FIG. 22—illustrates the macrophage population around the layered scaffold. There was little or no difference between the layered scaffold and the negative control (suture only) in terms of the macrophage population in surrounding tissue. Tissue sections were stained using iNOS for subtype M1 and mannose receptor for subtype M2.

Figure 23:
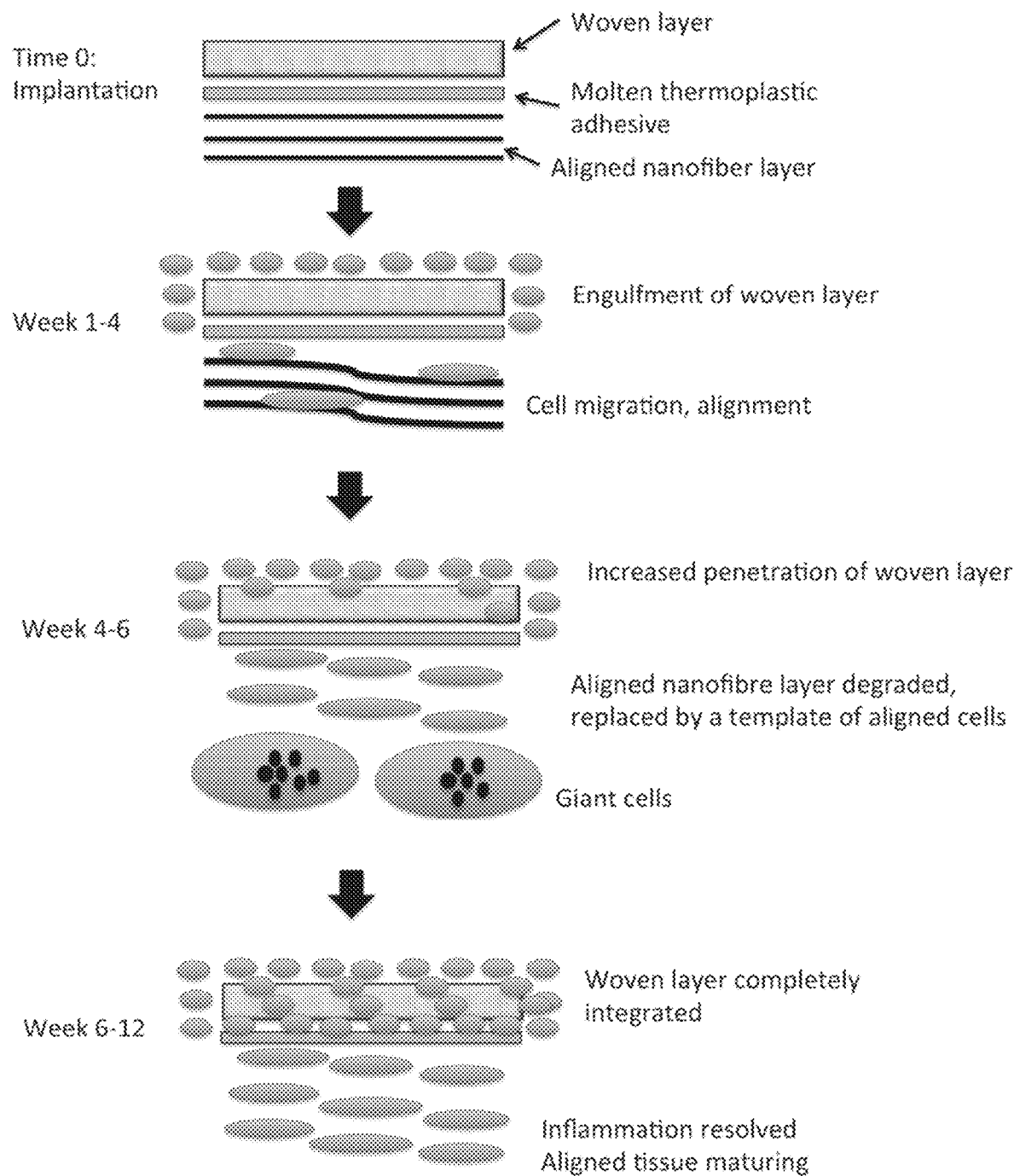

FIG. 23—is a schematic representation of tissue reaction to the scaffold based on in vivo observations

EXAMPLES

Example 1

The Fabrication of a Multi-Layered Patch for Rotator Cuff Repair: Combining Woven and Electrospun Fabrics Using Non-Destructive Binding The aim of this study was to produce a rotator cuff repair patch which possesses excellent mechanical as well as biological properties. This was to be achieved by combining a woven fabric, which will provide mechanical support, with a non-woven electrospun component, which will provide cues and guidance for native cells by way of presenting fine, nano-scale morphology.

Introduction

In this example, the use of a novel, biocompatible and non-destructive adhesive method for multi-layering electrospun materials and fabrics is investigated. This example first discusses the mechanical and in vitro properties of a patch consisting of a woven fabric linked to a non-woven electrospun component. The non-woven component is an oriented PDO electrospun scaffold, designed to provide excellent biological properties. The woven component is a plain weave of PDO monofilament and is designed to provide mechanical strength, suture retention (so that it prevents suture pull-out) and robust handling characteristics, so that it can be surgically sutured above the tendon to bone junction in the rotator cuff.

This example will then demonstrate that the method of adhesion preserves the surface morphology, the porosity and the biocompatibility of the electrospun material. For this purpose grid-like electrospun scaffold were stacked using the novel adhesive technique, and the migration of tenocytes through the resulting structure was studied.

Materials and Methods

Preparation of Electrospinning Solutions

Polymer solutions were prepared by dissolving Polydioxanone (PDO, 1.5-2.2 dl/g, Sigma-Aldrich Chemical Company Ltd., Dorset, UK) or polycaprolactone (PCL, Mw: 80,000 kDa, Sigma-Aldrich) into 1,1,1,3,3,3-hexafluoroisopropanol (HFIP, Apollo Scientific Limited, Cheshire, UK) at a concentrations of 9% (w/v) and 8% respectively. Solutions were agitated at room temperature on a roller for at least 24 hours to allow for complete dissolution of the polymers.

Electrospinning

PDO electrospun scaffolds were produced by electrospinning the PDO solution for 2 hours onto a drum rotating at 2000 rpm (to create oriented structures with a voltage of 8.2 kV. Lower rotation speed may be used (eg 100 rpm), which leads to random alignment of fibres. Higher rotation speeds (usually between 1000-5000) may lead to aligned fibres. PCL electrospun scaffolds were produced by electrospinning the PCL solution for 2 hours onto a drum rotating at 100 to 120 rpm and a voltage of 8.4 kV. PDO grids scaffolds were produced by electrospinning for 10 minutes onto a grounded nickel grid (width of 50 μm with spacing of 300×300 μm). To fabricate the unit of the "porous" layered constructs, a second electrospinning step was performed with the PCL solution for 1 minute. To fabricate the unit of the "non-porous" layered constructs (which will prevent cell migration), PCL was electrospun for 10 minutes onto the initial PDO grid. For each experiment the distance nozzle collector was set at 20 cm. All samples were detached from their collector using ethanol 70% and were stored in a dessicator. In an embodiment, PCL grids may be made using a patterned grounded nickel grid as collector. This can be done to improve the migration between the layers of aligned PDO.

Weaving

Plain weave structures were fabricated from PDO monofilaments (PDS II, 7.0, Ethicon, France) using a manual loom. To avoid fraying, edges of the samples cut from the main woven mat were molten by a very short contact with a hot plate at 150° C.

Adhesion of Woven and Non-Woven Components

The woven PDO layer was briefly brushed with a lab tissue soaked in hexafluoro-2-propanol (HFIP). The PCL layer (adhesive component) was then quickly placed onto the woven component and a gentle pressure was applied to help adhesion between the two components. (Note: This first step was advantageous for woven structures made of monofilament yarns having a diameter superior to 100 μm to improve the adhesion of PCL to the woven component. Woven fabrics made of yarns with smaller diameter and electrospun layers generally do not require this step).

The non-woven electrospun PDO layer was then placed on the PCL adhesive component and the assembly were maintained together with a gentle pressure while applying a heat treatment at 80° C. for 2 minutes. At that temperature, the PCL melted (Tm=65° C.) while the PDO remained intact (Tm=110° C.). Upon solidification during cooling, the PCL layer acts as an adhesive by entrapment of the PDO fibres from the different filaments. When adding more layers of electrospun PDO, pure PCL grids were sandwiched into each new layer of PDO and the previous one before the heat treatment. Heat treatment at that temperature might also slightly improve the mechanical properties of the patch, due to a gentle bonding of the PDO fibres.

Mechanical Testing

For each type of electrospun patch, 8 separate specimens were used, measuring 50 mm in length and 5 mm in width. Material testing dumbbell shapes were created. These 7 mm strips were 2 mm at their narrowest point to minimize midpatch failure as a result of stress rise at the patch-grip interface. 5 woven components with/without electrospun layer were also tested, measuring 20 mm in length and 2 mm in width. Environmental electron scanning microscope was used to measure the thickness of electrospun scaffolds.

The testing protocol was based on a modified version of previously published studies of patch mechanical properties (Derwin et al, 2006 & Chaudhury et al., 2012). Modified clamps were used to grip the ends of the patches, leaving a nominal grip-to-grip gauge length of 30 mm for electrospun scaffolds and 15 mm for woven PDO component. Specimens were tested to failure in tension using Zwick machine at rate of 0.5 mm/min until failure. Ultimate strength (MPa), breaking strain (%), was assesed. These values are independent of specimen shape, and thus, the measured material properties of patches can be compared with published data on other commercially available patches.

SEM

Biological samples were fixed and dehydrated prior being mounted on the stub. Samples were fixed in glutaraldehyde (2.5% v/v in deionised water) overnight. The fixative was removed and samples were rinsed twice in PBS before undergoing sequential dehydration in a graded ethanol series (40%, 70%, 90%, 95%, to 100% ethanol in deionised water, 10 minutes each step). Scaffolds were further dehydrated using hexamethylsilazane and were left inside the fume cupboard overnight for complete drying. Samples were stored in a dessicator until use. Samples were then mounted on an aluminium stub using a carbon adhesive disk and gold coated using a SC7620 Mini Sputter Coater System (Quorum Technologies Ltd, East Sussex). High resolution images were taken using a environmental scanning electron microscope (Carl Zeiss Evo LS15 Variable Pressure Scanning Electron Microscope).

Human Tendon Material, Donor Demographics and Clinical Data

Tendon tissue was obtained from the Oxford Musculoskeletal Biobank, with informed donor consent in full compliance with the National and Institutional ethical requirements, the United Kingdom Human Tissue Act (HTA).

Supraspinatus tendon samples were collected from patients with chronic degenerative rotator cuff tendinopathy and partial/full thickness supraspinatus tears. All patients were undergoing surgery for rotator cuff repair or subacromial decompression, during which tendon tissue was resected from the distal torn edge of the tendon and transferred immediately into a sterile tube containing DMEM F12 (Lonza, U.K.) for explanation. Tendon-derived cells for this study were obtained from 2 female donors aged 70-72 yr. Cells from each donor were used individually.

Tendon-Derived Cell Isolation and Culture

The tendon samples were cut into small uniform pieces under sterile conditions and transferred to 6 well plates (Corning, U.S.A.) supplemented with growth medium. Growth medium used was DMEM F12 containing 50% foetal bovine serum (FBS, Biosera U.K.) and 1% penicillin-streptomycin solution. Plates were incubated at standard conditions (37° C., 5% CO2) and growth medium was replaced every 2-3 days. Once cells had migrated from the explants, after approximately 7 days, the medium was refreshed with DMEM F12 containing 10% FBS. Cultures were maintained under these conditions until the wells reached confluence. The cells were then scraped and subcultured under the same conditions in 10 cm Petri dishes (Greiner, Germany) to allow proliferation. For all experiments, for consistency, and to avoid the phenotypic drift described after passage 5 (Poulsen et al., 2011; Yao et al., 2006), tendon derived cells were used in the second passage.

Cell Seeding on Materials

To assess growth on the electrospun patches, an alamarBlue assay was used as previously described (Hakimi et al., 2012). Briefly, electrospun patches were cut to size and suspended in 24 well cell crown inserts (Sigma). These were placed in 12 wells (Corning), sterilised using 70% Ethanol and dried overnight under sterile conditions in 40° C. Tendon-derived cells in passage 2 were then seeded into the inserts containing electrospun patches and allowed to attach for at least 12 hours.

Monitoring Cell Growth on the Patches

At selected time points, the cell crowns with the patches were transferred into fresh well plates containing complete medium with 5% alamarBlue (AbD Serotec, U.K.). Patches were transferred into fresh wells in every time point in order to exclude cells attached to the polystyrene well and measure exclusively the metabolism of cells attached to the patch. After two hours of incubation, duplicates of 100 µl medium samples from each well were transferred to white 96 well plates (Corning) for analysis in a SpectraMax Gemini microplate reader (Molecular Devices, U.K.), with fluorescence measured at 544 nm excitation and 590 nm emission wavelength. The remaining alamarBlue medium was removed and replaced with fresh standard medium.

Effect of Conditioned PBS on Cell Growth

To monitor the effect of exposure to the materials, PDO, PCL and PGA (the latter used as control as it degrades rapidly) at a concentration of 10 mg/ml was sterilised in 70% ethanol for 2 hours, dried and incubated for 1 month in sterile PBS at 37° C., 5% $CO_2$. After one month of incubation, $6 \times 10^3$ cells were seeded into 96 well plates in triplicates. Cells were allowed to attach over night, and after 12 hours, 10 ul of the PBS conditioned with materials was added to each well, leading to a final concentration of 0.5 mg/ml. Proliferation was measured after 5 days of exposure.

Fluorescence Microscopy

To visualise the cells using fluorescence microscopy, constructs were fixed in 10% formalin (Fisher Scientific) for 5 minutes and permeabilised using 0.1% Triton-X (Sigma-Aldrich) for 5 minutes. Consequently, cells were stained using rhodamine phalloidin (Invitrogen, UK) and DAPI nuclear counter stain (4',6-diamidino-2-phenylindole) according to manufacturer's instructions (Molecular Probes). Samples were visualised using a fluorescence or confocal microscope (Zeiss Axio Imager M1 or a Zeiss LSM710 NLO).

Gene Expression

Scaffolds were lysed in 1 mL of a tissue lyser, TRIzol® (Sigma-Aldrich, Dorset, UK) using the Gentle Macs tissue lyser (Milteny Biotec, UK). Following homogenization, the samples were centrifuged at 12,000×g for 10 min at 4° C. Samples were incubated at room temperature and 200 µl of chloroform was added, vigorously shaken for 15 sec, and centrifuged at 12,000 g for 15 minutes at 4° C. The upper aqueous phase (~50% of the total volume) was transferred to another tube. RNA was precipitated using 100% isopropanaol for 10 min followed by 10 min centrifugation at 12,000×g at 4° C. The RNA pellet was then washed with 1 ml of 70% ethanol. Finally, the extracted RNA was dissolved in RNase-free water and eluted. 1 µg of RNA was converted to cDNA using the First Strand cDNA Synthesis Kit (Roche, Germany) following the manufacturer's protocol. Real-time qPCR were performed using a ViiA7 (Life Technologies) with software version ViiA™ v1.2 (Applied Biosystems, USA), using Sybr Green (AB applied biosystems powerSYBR) and QuantiTect primer assays according to manufacturer instructions (QIAGEN). Cycling conditions were default parameters for relative quantification using Sybr green. Untreated cells were used as controls and GAPDH was used as a housekeeping gene. Data was analysed in terms of relative expression (RE).

In Vivo Study

The study was performed under a home office license and in accordance with institutional guidelines. Sixty Lewis rats were divided into 4 groups in which the infraspinatus was surgically transected 3 mm from its insertion. Tendons were repaired with a woven and electrospun polydioxanone patch and 5-0 Prolene sutures. Vicryl and Silk patches or a simple Prolene suture repair served as comparators. Animals were sacrificed at 1, 2, 4, 6 and 12 weeks to examine the biocompatibility of the implants. Immunohistochemistry was used to examine macrophage subpopulations and hematoxylin and eosin staining was used to assess foreign body giant cells and both analysed with a one-way ANOVA with significance set at p<0.05. Articular cartilage was scrutinised with semi-quantitative analysis. Hind paw inflammatory indices were used to determine the systemic effects.

Cell Migration Across Multi-Layered Patches

To demonstrate that the layering technique provides control over the porosity of the multi-layered electrospun material, cells were seeded onto three different electrospun sheets suspended in cell crowns as described above. The different materials were:

1. single sheet of porous grid-structure
2. A multi-layered (stack of 4) grid structure bound using thick, non-porous dense PCL sheets—layers were maintained together with a gentle pressure while applying a heat treatment at 80° C. for 1 minute.
3. A multi-layered (stack of 4) grid structure bound using fine, porous PCL sheets.

Approximately $5 \times 10^4$ cells were seeded directly onto each insert. A 12 well plate (Corning) was coated with fibrin gel, prepared from 25 µl of 10 mg/ml fibrinogen and 2 µl of 100 u/ml thrombin from bovine plasma (both Sigma-Aldrich), acting as a chemo-attractant to induce cells migration across the electrospun patch. The inserts were then transferred into the wells containing the fibrin, covered in growth medium and incubated for 5 days. Thereafter, an alamarBlue assay was carried out as described above to measure cell growth on the membranes and ESEM was used to evaluate cell presence on both sides.

ESEM

Samples were cut and mounted on an aluminium stub using a carbon adhesive disk. Samples were then coated, when necessary, with gold or platinum using a Cressington 208 HR sputtercoater (Vortex Control Systems, TX, USA) and high resolution images of the scaffolds were taken using a scanning electron microscope.

Statistical Analysis

Data are expressed as means±SEM. Graphs were created by the GraphPad Prism software version 5. Statistical analysis was performed with GraphPad Prism software. For all in vitro adhesion tests, at least two independent experiments were performed and the mean value was determined. For all studies, One-way ANOVA with post hoc Tukey testing was used to examine statistical differences between multiple groups. Unpaired t test was used to examine statistical differences between two independent groups. Results were considered significant when a P value of <0.05 was obtained.

Results

Fabrication of the Multi-Layered Patch

Our approach (FIG. 1A) involved the layering of electrospun and non-electrospun sheets using an electrospun thermoplastic adhesive. Compared to thermoplastic sheets or powder commonly used in the textile industry, the use of an electrospun mat enables uniform bonding with minimal quantities of polymer, as well as control over porosity. For the specific prototype presented here, an electrospun polycaprolactone (PCL) layer was placed between an electrospun PDO mat (E) and a woven PDO fabric (W). The construct was subjected to a heat treatment at 80° C. At this temperature the PCL layer melts but the PDO components remain intact, due to their higher melting temperature (PCL Tm=65° C.; PDO Tm=110° C.). Upon solidification, the molten PCL layer acts as an adhesive, trapping the PDO fibres. The resulting textile (FIGS. 1D and E) is a layered composite of the woven and electrospun components, which are separated by a fine, molten PCL film. It is worth noting that the electrospun aligned PDO fibres presented a crimped, tendon-like morphology (FIG. 1H). Crimped nanofibres have been previously reported, with some purposefully manufactured using air-driven electrospinning, and others spontaneously self-crimping after standard electrospinning. As can be seen in the image presented here (FIG. 1), PDO aligned mats presented a subtle self-crimping effect, maintaining an overall aligned and highly organised appearance compared to the more coiled, disrupted appearance previously reported. Importantly, the bonding method is non-destructive, and a micrograph of the electrospun side post-manufacturing (FIG. 1F) shows that the original aligned/crimped pattern has been maintained.

Morphology of the Novel Multi-Layered Patch

With reference to FIG. 2, SEM images show the assembled construction, with the woven monofilament layer well adhered to the nanofibrillar electrospun component using the PCL as a heat-responsive glue. With reference to FIG. 3, ESEM images showing the gross appearance of the electrospun PDO sheet component (a) and woven PDO monofilament component (B) of the patch prior to assembly.

Mechanical Studies:

To determine the effect of the layering and bonding on the mechanical properties of the scaffold, tensile and suture retention tests were carried out using Zwick tensile machine (5 kN) and a Deben tensile stage (600N). Tensile strength, % strain at failure and Young's modulus of the layered scaffold and its components were calculated. As expected, the combination of the woven and electrospun layers resulted in a much stronger scaffold (at least 20 fold, FIG. 5A) compared to the electrospun layer on its own. Moreover, it confirmed that the bonding process did not reduce the strength of the woven PDO layer (63.72±10.56 MPa). The maximum stress of the assembled patch (65.76±10.32 MPa) was not significantly different from that of the woven component either (FIG. 5B-5C). Experiments were then undertaken to better match the suture pull out between the layered scaffold and human tendon (FIG. 5D-F). Comparing the weave patterns 'plain' (P, FIG. 5G) and 'twill' (T, FIG. 5L), it was found that ultimate tensile strength was not significantly different between these weaves (65.76±10.32 and 73.9±8.79), but suture retention by the twill weave was significantly higher (167±34). The twill woven layer was capable of tolerating forces exceeding those reported for the human infraspinatus tendon (ultimate stress=15-30 MPa and force during maximum contraction ~196N (55, 56)). The ability to vary weave patterns and successfully match the scaffold's mechanical properties to the desired tissue and application holds a potential to develop additional prototypes.

The mechanical properties of the electrospun component can be increased by sticking several layers together, as shown in FIG. 6. The maximum stress values were significantly different between 1, 4 and 8 layer scaffolds. Moreover, 4 layer scaffolds showed highest strain at failure (%). The mean thicknesses of 1 layer, 4 and 8 layer electrospun scaffolds are shown in FIG. 7.

Cell Growth on the Patches and Cytotoxicity of the Materials

With reference to FIG. 8, growth of tendon-derived cells on single and multilayered PDO scaffolds is shown over 21 days, measured using AB (n=3). There was no significance difference in cell growth (relative to day 1) between multilayer and single layer constructions. Therefore, stacking electrospun layers does not modify the way cells grow and survive on them.

With reference to FIG. 9, adhesion of tendon derived cells to PDO and PCL revealed that there were no statistical differences in viable cells attached to these materials 24 hours after seeding. Adhesion was monitored using Alamar-Blue. Therefore, stacking electrospun layers does not modify the way cells adhere to them.

With reference to FIG. 10, growth of tendon-derived cells on PCL and PDO scaffolds is shown over 14 days, measured using AB (n=4). There was no statistical difference in cell growth (relative to day 1) between these two materials. This supports the suggestion that PDO and PCL are similarly compatible, and that adding PCL to the PDO construct (in order to create multi-layers) should not modify the way cell interact with the scaffold.

With reference to FIG. 11, cells exposed to PCL, PDO and PGA showed differential responses to these electrospun materials. Whilst PGA-exposed cells showed reduced cell growth compared to PBS control, there was no growth inhibition in cells exposed to PCL and PDO conditioned PBS. PBS was conditioned for 1 month and cells were exposed to a maximum of 0.5 mg/ml material. This suggests that PDO and PCL are compatible and non-toxic for tendon derived cells, compared with a faster degrading polymer such as PGA.

The Effect of the Component Layers on Cell Behavior In Vitro

In further studies the contribution of the electrospun component in terms of cell attachment and growth was evaluated in a series of studies, where the woven layer on its own (W) was compared to the complete layered scaffold with the aligned, electrospun mat (W+E). These studies showed that viable cells attached and proliferated on both of these substrates, but cell numbers were significantly higher on the electrospun component at both the 1 day and 7 day time points (FIGS. 12A and B). This trend was further confirmed by SEM micrographs of the cells on the different surfaces at 1 hour, 3 hours and 24 hours after seeding. The images demonstrated a more rapid trapping and flattening of cells on the electrospun surfaces. Cells attached to the woven structure tended to wrap around filaments or settle into the niches and gaps formed by the weaving process between filaments (FIG. 12C). In contrast, cells attached to the electrospun layer presented an even distribution and coverage of the mat and appeared embedded in the electrospun matrix. Quantification of cell dimensions, using fluorescence images of the cell cytoskeleton after 3 days in culture (FIG. 12C-G), demonstrated that the addition of an electrospun layer modulated cell length, width and orientation. Cells were significantly longer, narrower and more orientated on the electrospun surface compared with the woven layer (FIG. 12C-G), although there was a degree of orientation on the woven component, possibly due to groves from the extrusion process (visible in FIG. 13A). Micrographs of long-term cultures (2, 4, and 8 weeks, FIG. 13B) showed gradual increase in cell coverage for both the layered scaffold and the woven component, with cells forming loose networks on the woven mat and dense, well-embedded arrays on the electrospun component. Up to week 4, the aligned electrospun mat is still visible and displaying a well ordered aligned morphology. On week 8, it appears that the cell networks on the woven layer are expanding to cover the gaps in a more visible manner.

Cell Migration Across Multi-Layered Grid Patches

To demonstrate that the flexibility of the layering technique, and the fact that it preserves the morphology and porosity of the PDO electrospun material, cells were seeded onto a 4-layer construct made out of electrospun grids. FIG. 14 indicates that, depending on the amount of PCL glue present between the layers prior the heat treatment, the scaffold material can be adjusted to be porous or non-porous (subfigures 14B and C). Only a little amount of PCL is necessary to allow efficient adhesion between the layers of the scaffold.

The Effect of the Component Layers on Cell Phenotype

Figure 17:
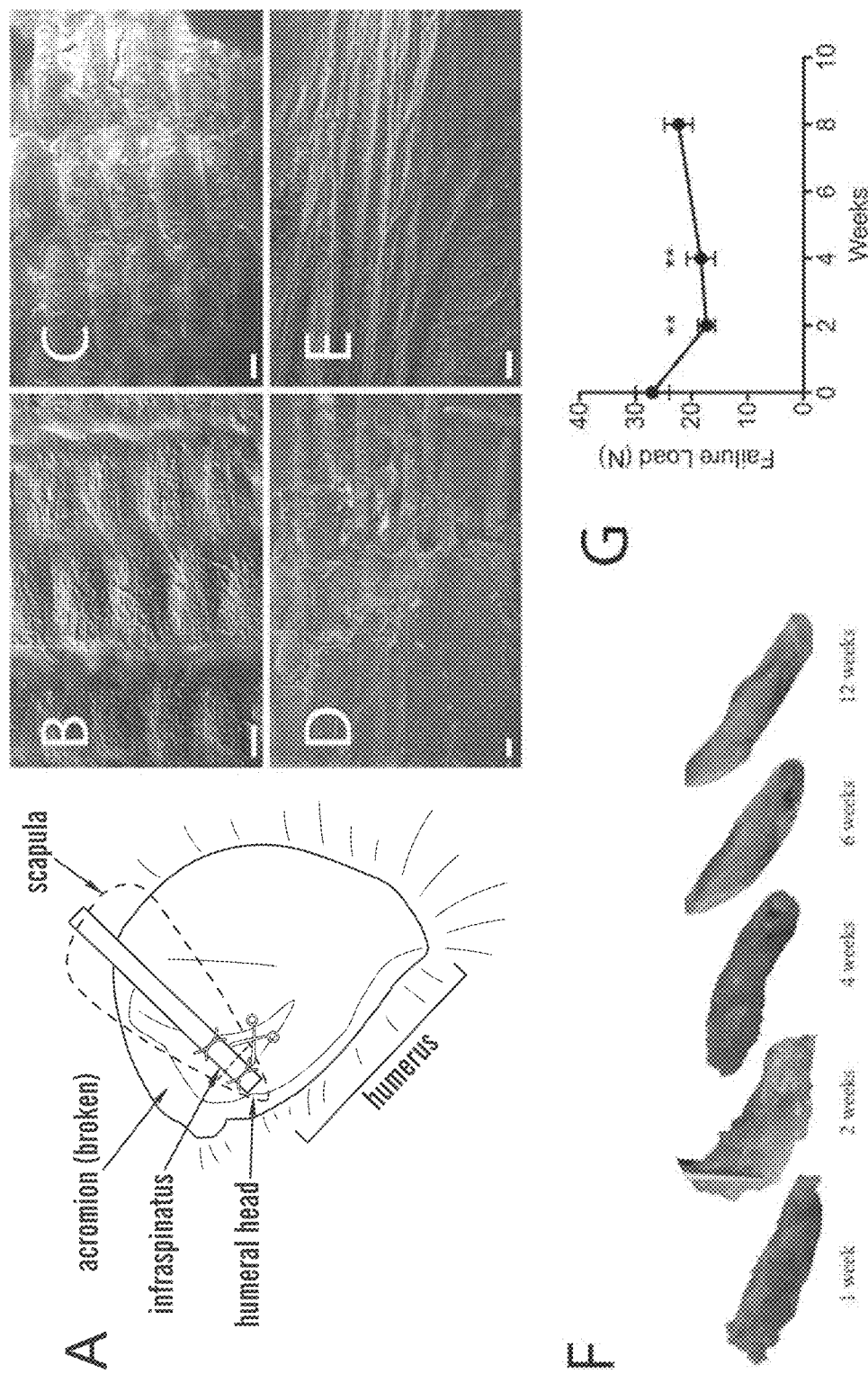

The observation that the addition of the aligned electrospun layer modulated cell shape, which is highly linked to cell phenotype, prompted an investigation into whether there was any effect on cell phenotype. RNA expression of ten different genes was measured using real time PCR (FIG. 16). The markers were chosen to represent possible effect on extracellular matrix production (Collagen I and Collagen III), the pericellular matrix (Collagen VI and fibrillin 1), cell-matrix adhesion (fibronectin and integrin $\beta1$), and markers of shape ($\beta$-actin) and cell-cell contacts (Cadherin 11). Collagen I, collagen VI, fibronectin and integrin $\beta1$ were at the basal level for monolayers and did not significantly differ between the populations grown on the woven component and the layered scaffold. Relative expression of Collagen I was slightly but not significantly higher on the layered scaffold. Significant differences in the expression of collagen III, fibrillin1, $\beta$-actin and cadherin 11 were measured, and these four genes were observed to be significantly more highly expressed on the layered scaffold Biocompatibility and Cell Infiltration In Vivo The biocompatibility and cell infiltration of the patch after implantation in a rat's shoulder was assessed. This animal study was performed to demonstrate safety rather than efficacy of the layered design. Preliminary in vivo evaluation of the assembled patch was carried out for periods of 1, 2, 4, 6 and 12 weeks. FIG. 17 shows the placement of the patch directly above the infraspinatus in the rat's shoulder. Upon gross examination it was noted that all animals had fibrous capsules around the repaired tendons, which increased in size up to 2 weeks and then gradually decreased. It was also noted that the implant remained intact for the duration of the study. No delamination or separation of layers occurred. At the later time points of 6 and 12 weeks there was a fibrous tissue tightly adhered to the material, and the woven pattern was not visible on gross examination and scanning electron microscopy (FIG. 17). Mechanical evaluation of the explanted scaffold revealed a significant initial reduction in strength up to 2 weeks and an increase in mechanical strength thereafter up to week 8 (FIG. 17), indicating significant tissue ingrowth or neo-tissue formation.

Histological sections of the layered scaffold and the surrounding tissue demonstrated the extent of foreign body response and cell infiltration into the patch. A suture-only repair with non-degradable Prolene was used as negative control, and a repair with a woven vicryl mat (polygalactin 910) was used as a positive control. Hematoxylin-eosin stained sections (FIG. 18, FIG. 19 and FIG. 20) demonstrated that on the electrospun side of scaffold cells elongated in well-oriented arrays within bundles of pale fibres, possibly the electrospun material (most visible on week 1). This relatively organized tissue appeared thicker and more pronounced after 4 weeks, although it is harder to distinguish any pale electrospun-like fibres at this time point. At the 6 and 12 week time-point there are still clear arrays of well-oriented cells in the vicinity of the scaffold. Histological sections were also examined for the formation of multinucleated foreign body giant cells (FBGC). At week 4 there were higher numbers of FBGC around the experimental patch compared to the suture-only control (FIG. 21), but at all other time points FBGC levels were comparable to the suture-only control. The increase in FBGC at 4 weeks was observed in parallel to the gradual disappearance of the electrospun component, which was only sparsely visible in the tissue by week 6. Over the 12 week period FBGC numbers were lower around the layered scaffold compared to the positive control (Vicryl). Experiments were also carried out to characterise macrophage presence and sub-types around the repair site. Histology sections stained for the inducible isoform of nitric oxide synthase (iNOS), a marker of macrophage subtypes M1 (killer macrophages associated with infections) and mannose, a marker of macrophage subtype M2, (associated with wound healing), are presented at FIG. 22. Evaluation of these markers revealed similar ratios of M1 and M2 to the total number of counted cells between the experimental group and the negative control, compared to elevated ratios of both macrophage sub-types around the positive control (FIG. 21).

And overview of the tissue reaction to the layered scaffold in vivo, based on the gross and histological observation is presented in FIG. 23.

Discussion

In the study presented here, a multi-layered novel patch, designed to provide mechanical strength and biological guidance, has been tested. Both components of the patch were made of polydioxanone (PDO), a biocompatible polymer that degrades by hydrolysis. The woven component was assembled using a traditional loom from monofilaments or electrospun yarns. The non-woven component was formed using electrospinning, thus creating a highly porous structure which allows effective trapping of cells and protein solutions. Electrospinning also allows the entrapment of bioactive factors (such as growth factors or vitamins) during the production of the patch, thus incorporating the active ingredients within the fibres.

The adhesive layer, placed between the woven and non-woven layer, was made of another biocompatible and biodegradable polymer, polycaprolactone (PCL). During the heat treatment performed at around 80° C., PCL melts (Tm=65° C.) while PDO remains intact (Tm=110° C.). This allows binding of the fibres from both PDO components into the PCL layer, which acts as an adhesive upon solidification.

In this study, it has been shown that varying the thickness and pattern of the adhesive PCL layer results in porous or non-porous structures. For example, using a fine electrospun sheet of PCL to attach several layers of electrospun PDO, if thin enough, the bonded PCL will preserve the initial porous morphology of the PDO construct.

The mechanical tests clearly reveal the importance of the woven component, which is more than 20 times stronger than the electrospun component.

Results presented above demonstrate that cells could migrate a cross such a multi-layered construct, and that the surface appearance of the outermost layer, which may be used as a guiding template for tendon healing, has remained intact.

It is also shown that both PCL and PDO component are compatible, and present similar cell attachment and growth patterns, thus minimising the risk of modifying cell response to a more complex structure combining these two elements.

Results presented here confirmed this predicted stability, showing good cell survival on the construct for up to 8 weeks in vitro and good integrity and tissue integration up to 12 weeks in vivo, with the construct appearing intact and with no visible delamination or detachment of layers taking place within this timeframe.

CONCLUSIONS

A novel method of binding varying layers of medical textiles for tissue engineering is presented. This adhesive method is biocompatible, minimally destructive to nano-patterns (such as electrospun surfaces) and enables control over porosity by controlling the morphology of the adhesive layer. A prototype of tendon repair patch produced using this method has also been presented.

In this example, a robust, woven component, which would provide mechanical support to the healing tendon, was combined with a fine nanostructured sheet, which is highly inductive for cells. Results show that the resulting material retained strength, safety and nano-patterns, and may be useful for the augmentation of tendon tear in the rotator cuff.

REFERENCES

Saino E, Focarete M L, Gualandi C, Emanuele E, Cornaglia A I, Imbriani M, Visai L (2011) Effect of Electrospun Fiber Diameter and Alignment on Macrophage Activation and Secretion of Proinflammatory Cytokines and Chemokines. *Biomacromolecules* 12: 1900-1911

Hakimi, O., Murphy, R., Stachewicz, U., Hislop, S., and Carr, A. J. (2012). An electrospun polydioxanone patch for the localisation of biological therapies during tendon repair. European cells & materials 24, 344-357.

Moffat, K. L., Kwei, A. S., Spalazzi, J. P., Doty, S. B., Levine, W. N., and Lu, H. H. (2009). Novel Nanofiber-Based Scaffold for Rotator Cuff Repair and Augmentation. Tissue Eng Part A 15, 115-126.

Raghavan, S. S., Woon, C. Y. L., Kraus, A., Megerle, K., Pham, H., and Chang, J. (2012). Optimization of Human Tendon Tissue Engineering: Synergistic Effects of Growth Factors for Use in Tendon Scaffold Repopulation. Plast Reconstr Surg 129, 479-489.

Poulsen R C, Carr A J, Hulley P A (2011) Protection against glucocorticoid-induced damage in human tenocytes by modulation of ERK, Akt, and forkhead signaling. *Endocrinology* 152: 503-514.

Yao L, Bestwick C S, Bestwick L A, Maffulli N, Aspden R M (2006) Phenotypic drift in human tenocyte culture. *Tissue engineering* 12: 1843-1849.

Chaudhury S. Holland C, Thompson M, Vollrath F, Carr A J, Tensile and shear mechanical properties of rotator cuff repair patches, Journal of Shoulder and Elbow Surgery, Volume 21, Issue 9, September 2012, Pages 1168-1176.

Derwin, k; Baker, A; Spragg, R K; Leigh, D. R; Iannotti J. P, Commercial extracellular matrix scaffolds for rotator cuff tendon repair Biomechanical, biochemical, and cellular properties, *J Bone Joint Surg Am,* 2006 Dec. 1; 88(12):2665-2672. doi: 10.2106/JBJS.E.01307

We claim:

1. A method of producing a scaffold for tissue repair, the method consisting of the steps of:
   forming a layered material by laying a single woven material layer onto two or more porous biodegradable polymer fibre layers such that there is a biodegradable adhesive component between each layer, and the two or more porous biodegradable polymer fibre layers are only bonded together via an adhesive component comprising electrospun fibres that are substantially arranged in a grid pattern; and
   heating the layered material to a temperature (Tm) above the melting temperature of the adhesive component but below the melting temperature of the material layer and the two or more porous polymer fibre layers, and then cooling the layered material to a temperature below the melting temperature of the adhesive component, thereby bonding the layered material together to form a biodegradable scaffold.

2. The method of claim 1, wherein pressure is applied to the layered material in order to press the layers together during the heating and cooling.

3. The method of claim 1, wherein the layered material is heated to a temperature of between about 60° C. and about 100° C.

4. The method of claim 1, wherein the layered material is heated for at least about 30 seconds prior to cooling.

5. The method of claim 1, wherein the scaffold is impregnated, seeded or coated with an agent and/or cells.

6. The method of claim 1, wherein the material layer consists of a woven component that is provided by weaving a fibre, yarn, thread or monofilament into a weave, or a plain weave.

7. The method of claim 6, wherein the fibre, yarn, thread or monofilament of the woven component is formed by spinning; and optionally by electrospinning.

8. The method of claim 1, wherein the polymer fibre layer is formed by spinning; and optionally by electrospinning.

9. The method of claim 8, wherein the electrospinning is onto a grid.

10. The method of claim 7, wherein agent is incorporated in the fibre, yarn, thread or monofilament of the woven component during the spinning process.

11. The method of claim 8, wherein an agent is incorporated in the non-woven polymer component and/or adhesive component during the spinning process.

12. The method of claim 1, wherein the material layer, and/or the polymer fibre layer are formed from PDO.

13. The method of claim 1, wherein the adhesive component is formed from PCL.

14. The method of claim 1, wherein the adhesive component between the material layer and the two or more polymer fibre layers is non-porous.

* * * * *